US010008373B1

(12) United States Patent
Carr

(10) Patent No.: US 10,008,373 B1
(45) Date of Patent: Jun. 26, 2018

(54) IMPEDANCE SPECTROMETER WITH TEMPERATURE-CONTROLLED MICRO-PLATFORM

(71) Applicant: William N Carr, Ralegh, NC (US)

(72) Inventor: William N Carr, Ralegh, NC (US)

(*) Notice: Subject to any disclaimer, the term of this patent is extended or adjusted under 35 U.S.C. 154(b) by 0 days. days.

(21) Appl. No.: 15/805,698

(22) Filed: Nov. 7, 2017

Related U.S. Application Data

(63) Continuation-in-part of application No. 15/727,249, filed on Oct. 6, 2017, and a continuation-in-part of application No. 15/626,151, filed on Jun. 18, 2017, now Pat. No. 9,817,130.

(51) Int. Cl.

| | | |
|---|---|---|
| *G01T 1/02* | (2006.01) | |
| *H01J 49/02* | (2006.01) | |
| *G01N 27/414* | (2006.01) | |
| *H01J 49/00* | (2006.01) | |
| *G01R 27/26* | (2006.01) | |
| *G01R 33/00* | (2006.01) | |

(52) U.S. Cl.
CPC ........ *H01J 49/025* (2013.01); *G01N 27/4146* (2013.01); *G01R 27/26* (2013.01); *G01R 33/0023* (2013.01); *H01J 49/0027* (2013.01)

(58) Field of Classification Search
CPC ............. G01N 27/127; G01N 27/4146; G01N 33/497; G01N 33/0037; G01N 33/004
See application file for complete search history.

(56) References Cited

U.S. PATENT DOCUMENTS

| | | | | |
|---|---|---|---|---|
| 7,948,041 | B2* | 5/2011 | Bryant | G01N 27/127 257/414 |
| 9,006,857 | B1* | 4/2015 | Carr | H01L 27/14601 257/12 |
| 9,103,775 | B2* | 8/2015 | Bradley | B82Y 10/00 |
| 2011/0263036 | A1* | 10/2011 | Blauw | G01N 27/4146 436/149 |

OTHER PUBLICATIONS

Cui et al., "Nanowire nanosensors for highly sensitive and selective detection of biological and chemical species", 2001, Science, vol. 293, pp. 1289-1292.*

* cited by examiner

*Primary Examiner* — Kiho Kim

(57) ABSTRACT

An impedance spectrometer comprised of a thermal microplatform supported with phononic structured nanowires disposed within a micromachined structure is provided to identify, monitor and characterize a gas, vapor, solid or liquid analyte. The impedance sensor and analyte sensing element in embodiments are formed from a semiconductor SOI starting wafer.

21 Claims, 20 Drawing Sheets

PRIOR ART

PRIOR ART

IMPEDANCE SPECTROMETER WITH TEMPERATURE-CONTROLLED MICRO-PLATFORM

STATEMENT OF RELATED CASES

This case is a continuation-in-part of U.S. Patent Application No. 2017/0237466 filed Feb. 16, 2017, U.S. Patent Application No. 2017/0248533 filed Feb. 27, 2017, U.S. patent application Ser. No. 15/626,151 filed Jun. 24, 2017, and U.S. patent application Ser. No. 15/727,249 filed Oct. 6, 2017. These cases are incorporated herein by reference. This case claims benefit of the following provisional applications:
   (1) U.S. provisional application No. 62/493,147
   (2) U.S. provisional application No. 62/106,805
   (3) U.S. provisional application No. 62/210,888
   (4) U.S. provisional application No. 62/043,376.

If there are any contradictions or inconsistencies in language between this application and the cases that have been incorporated by reference that might affect the interpretation of the claims in this case, these related claims should be interpreted to be consistent with the language in this case.

FIELD OF THE INVENTION

This invention relates to an impedance spectrometer comprised of a micromachined thermal micro-platform supported with phononic nanowires.

BACKGROUND OF THE INVENTION

Micro-platforms comprised of sensors have been developed for many applications during the past 30 years. Some of the earliest micro-platforms were physically configured as infrared detectors fabricated using semiconductor wafers. Other micro-platforms have been physically configured with mechanically-actuated support structures. Applications for micro-platforms include providing an environment for sensing of thermal, photonic, and electrical effects involving the platform payload and its exposed surrounding environment.

Most applications for micro-platforms involving a thermal micro-platform are enhanced when the thermal isolation of the platform is increased. There is a need for micro-platforms wherein supporting structures have a reduced thermal conductivity. structures. Specific configurations for micro-platforms with increased thermal isolation from a surrounding support platform are needed to make possible sensors of significantly improved performance. Many applications also are enhanced using support structures of the micro-platform with adequate electrical conductivity.

Prior art micro-platforms with increased thermal isolation from a surrounding support platform are disclosed in U.S. Pat. No. 9,236,552 and U.S. Pat. No. 9,722,165. These micro-platforms are supported by semiconductor nanowires with phononic structures that reduce thermal conductivity and provide an increased thermal isolation for sensing, heating and cooling structures disposed on the micro-platform.

In many applications, it is difficult to obtain a highly specific impedance signature from a particular analyte when sensor measurements relating to bulk permittivity are restricted to a specific temperature and at a moment in time. There is a need for thermal micro-platforms providing a means for sensing an analyte at a specific temperature or over a range of temperatures wherein the analyte sensing temperature is controlled with reduced electric power.

Prior art chemical and biological sensors comprising electromagnetic couplers and resonant LCR structures exposed to an analyte of interest are disclosed in U.S. Pat. No. 9,638,653 and U.S. Pat. No. 9,678,030. Prior art does not disclose an impedance spectrometer comprised of a thermal micro-platform supported with phononic structured nanowires disposed within a micromachined structure which in embodiments is formed from a starting semiconductor-on-insulator wafer.

SUMMARY OF THE INVENTION

The present invention provides an impedance spectrometer for identifying, monitoring and characterizing a gas, vapor, solid or liquid analyte of interest. The spectrometer is comprised of an impedance sensor and an impedance analyzer sensitive to the bulk electromagnetic permittivity of an analyte. The impedance analyzer is connected by a wired or wireless link to the impedance sensor. All or a portion of the impedance sensor is disposed on a pixel die comprised of a micro-platform. In embodiments, the impedance sensor may include both a micromachined micro-platform and a surrounding polymer or ceramic circuit board. The impedance sensor is comprised of one or more analyte sensing elements disposed on one or more micro-platforms wherein each analyte sensing element is exposed to an analyte.

The salient features of the impedance spectrometer include:
   a thermal micro-platform formed of a device layer and supported by nanowires wherein the nanowires are partially disposed on a surrounding support platform;
   nanowires physically configured with nano-dimensioned phononic structures to provide a reduction in thermal conductivity;
   wherein the thermal micro-platform is comprised of one or more of analyte sensing elements, one or more of temperature sensing elements and one or more of temperature control elements; and
   wherein each analyte sensing element is coupled with an analyte through a resistive coupling or an electric, magnetic or electromagnetic field coupling.

The micro-platform: The thermal micro-platform is comprised of an analyte sensing element, a temperature control element and a temperature sensing element. In embodiments, the micro-platform is formed from an SOI starting wafer. The SOI wafer, in embodiments, may comprise a silicon SOI starting wafer processed at wafer scale. The impedance sensor elements are disposed on one or more micro-platforms disposed on one or more die providing sensitivity to one or more analytes. Dicing of micro-platforms is performed as a post-cleanroom step prior to die packaging. Individual die with micro-platforms may be comprised of integrated circuits disposed on the surrounding support platform.

The micro-platform is physically configured with an appropriate sub-micron thickness and appropriate area to provide an isotherm across the platform. The thermal heat capacity of the micro-platform and the thermal conductivity of the supporting nanowires determine the thermal time constant for the platform. The thermal time constant in embodiments varies from microseconds to seconds.

Relating now to the nanowires: The micro-platform is supported by semiconductor nanowires comprised of phononic structures which scatter and/or resonate heat conducting phonons thereby reducing thermal conductivity along the length of the nanowire. In embodiments, nanowires are comprised of a semiconductor device layer.

The dimensions of phononic structures are configured to not limit the scattering range for electrons and thereby have a minimal effect on the bulk electrical conductivity of the nanowire. In embodiments of this invention, a first nanowire film is comprised of a semiconductor where the difference in mean free path for phonons and electrons is significant. Typically, in embodiment nanowires, the mean free path for electron ranges from less than 1 nm up to 10 nm. The mean free path for phonons that dominate the thermal transport within nanowires of the present invention is within the range 20 to 2000 nm, significantly larger than for electrons. In embodiments comprising silicon nanowires, phononic structures with dimensional separations of over 10 nm are preferred.

In some embodiments, phononic scattering and/or resonant structures are created by patterning the first layer of a nanowire with physical holes using submicron lithography. This particular type of texturing creates patterned "holey" structure into the first layer of nanowires and reduces thermal conductivity along the length of the wire.

In some embodiments, the nanowire first layer film is created using a solgel, electrochemical or multi-source evaporation/sputtering process to deposit a film which upon subsequent annealing budgets provide a porous or particulate-structured film of nanocrystals with phononic scattering structure. In other embodiments the nanowire first layer is created using a chemical vapor deposition (CVD) process. In these embodiments phononic scattering structures of desirable dimensions are created "in situ" within the nanowire, somewhat randomly disposed. These embodiments provide a phononic nanowire wherein the dimensions of the nanowire are patterned using lithographic or e-beam machining tools. Synthesis of thin films of nanometer thickness with porous or particulate-structured film is well known to those familiar with the art.

In embodiments, the nanowire first layer is a semiconductor selected from a group including, without limitation, Si, Ge, SiGe, $ZnO_2$, GaAs, $Ga_2O_3$, GaN, $Bi_2Te_3$, $CoSb_3$, $SO_2$, $AsH_3$, $Sb_2Te_3$, $La_3Te_4$, SiC, GaN, $(Bi_{1-x}Sb_x)_2Te_3$ and binary/ternary alloys thereof.

In embodiments, nanowires are comprised of multiple, stacked films in addition to the semiconductor first film. These additional films are dielectrics and/or nano-thickness metal films structured to minimize parasitic thermal conduction. In some embodiments a metal film of nano-thickness provides a desirable additional electrical conductance in addition to the electrical conductance of the first nanowire layer for signals or power through the nanowire. In embodiments, a dielectric film provides an electrical insulation between a metal film and the first semiconductor film of the nanowire providing two separate, isolated electrical connections with structures on the micro-platform In embodiments, the nanowire is physically configured of a sandwich structure comprised of a second layer. This second layer is an ALD metal of nanometer thickness selected from a group including, without limitation, Pt, W. Pd, Cu, Mo and Al providing an increased electrical conductivity. The second layer may be patterned over an area continuing through the nanowire and onto the micro-platform. In embodiments, a thin film ALD metal within a nanowire may connect further onto a metal or semiconductor active thermal heating element disposed on the micro-platform.

In other embodiments, a nanowire is a sandwich structure comprised of a third layer of a dielectric material selected from one or more of, without limitation, silicon nitride, silicon oxynitride, aluminum oxide, silicon dioxide and PDMS to provide electrical isolation and/or a reduction in mechanical stress. The third layer may extend beyond the nanowire and over the micro-platform providing a biaxial compensating stress, often a tensile stress, to reduce overall stress across the micro-platform.

Relating now to the impedance analyzer: In embodiments, a direct-wired connection is provided between the impedance analyzer and the impedance sensor through bonding pads, contact solder bumps or vias. In these embodiments, the analyzer may be configured to provide one or more of the maximum of the real part of the impedance, the magnitude of the imaginary part of the impedance, the anti-resonant frequency of the imaginary part of the impedance, the zero-reactance frequency and with readings encompassing a range of signal power levels at temperatures over a period of time. In embodiments, the impedance analyzer is comprised of a controller programmed with a decision matrix based on many sensed datapoints permitting identification and monitoring of the analyte.

In other embodiments, the spectrometer is of a wireless-type wherein the impedance analyzer communicates with the impedance sensor by wireless means. In these embodiments, the impedance analyzer is comprised of an RFID interrogator reader further comprised of an RF transmitter and receiver magnetically or electromagnetically-coupled with the impedance sensor. In this embodiment the impedance sensor is typically comprised of an RF transponder comprised of a resonant LCR antenna. In other wireless embodiments, the LCR antenna without a connected transponder is interrogate by the impedance analyzer. In wireless embodiments, at least one resonant LCR sensor antenna is exposed to the analyte. The resonant antenna provides an analyte sensing element wherein it is detuned in varying degrees by resistive or field-coupling with the analyte. The RFID receiver provides measurements of a return signal strength intensity RSSI and/or phase delay PD from the RF transmitter signal. In embodiments, the RSSI signal received by the impedance analyzer is a reflected signal originating from the impedance analyzer. In the wireless embodiments, impedance sensor is interrogated by the impedance analyzer at one or more RF frequencies and one or more RF power levels over time.

In some embodiments of the wireless type comprised of an RFID interrogator reader, the impedance sensor is comprised of integrated circuit components such as a microcontroller which tunes the resonant frequency of the sensor antenna within the impedance sensor. In embodiments, the impedance sensor may be comprised of passive and/or active integrated circuitry. An example of an RF transponder sensor comprised of an integrated circuit RF energy harvesting circuit and an integral antenna tuner is referenced in U.S. Patent Application 2017/0237466 filed Feb. 16, 2017.

Relating now to the impedance sensor: The impedance sensor is comprised of an analyte sensing element, a temperature control element and a temperature sensing element. The analyte sensing element is resistively-coupled or field-coupled with the analyte. All or a portion of the impedance sensor is exposed to the analyte and comprised of one or more of a resistor, inductor, capacitor, and antenna. The complex impedance of the impedance sensor is affected by the real and imaginary permittivity components of the analyte.

The impedance sensor may be a resonant or non-resonant type. For a resonant impedance sensor, electrical parameters including resonant frequency $f_o$ and quality factor Q with associated measurement parameters provide a means for identification and monitoring of the analyte. The electrical impedance of the impedance sensor is analyzed by the impedance analyzer to identify and monitor an exposed analyte.

Relating now to the temperature control elements: In embodiments, the temperature of the micro-platform may be controlled over a temperature range including both heating and cooling. The temperature control element may be a resistive heater or a thermoelectric cooling device disposed on the micro-platform. The heater may be comprised of a resistive metal film or a semiconductor film. In embodiments, the heater of metal film is typically comprised of one or more of W, NiCr, Pd, Ti, Cu, Pt, and Al of nanometer thickness with an underlying ALD adhesion enhancer such as Ti or Cr. In embodiments, the semiconductor heater is formed of the diffused region of a semiconductor diode created within the device layer of the starting SOI wafer wherein the diode is operated with a reverse junction bias to provide electrical isolation from the surrounding micro-platform region. In other embodiments, the thermal heating element is graphene or nanotubes including carbon nanotubes with appropriate resistivity.

In embodiments, the temperature control element is a resistive heater which heats the micro-platform to provide a means for outgassing the analyte sensor element. Thermal cycling provided by the heater provides a mechanism for the resetting the analyte sensor element impedance condition. An alternative means for resetting the analyte sensor element is to wait longer at room temperature for outgassing and equilibration which is often undesirable.

In embodiments, wherein the micro-platform is cooled with a thermoelectric temperature control element, heat is removed from the platform through the nanowires to the surrounding support platform. Cooling is provided by one or more thermoelectric Peltier thermoelectric devices. The thermal energy transport rate is proportional to power delivered to the Peltier device from an external source. Each thermoelectric device is comprised of one or more first junctions disposed on the micro-platform and second junctions disposed on the surrounding support platform. The first and second junctions are physically connected by the electrically conducting semiconductor nanowires. Each thermoelectric cooling device is typically comprised of a plurality of first junctions.

Relating now to the temperature sensor element: In embodiments, a single resistive heater may also provide a temperature sensing element when operated with reduced power level and with appropriate sensing/control circuits. The resistive element can be powered through a potentiostat which provides a programmed current source and a voltmeter connected across the resistive element. The current source powers the resistive element for heating and sensing and the voltmeter senses the temperature.

In embodiments, the temperature sensing element may also be a thermoelectric device operated in the Seebeck mode to provide a precision measurement of micro-platform temperature. The Seebeck sensing element generates a voltage proportional to the temperature difference between the on-platform junction and the off-platform junctions. Since Peltier and Seebeck effects are thermodynamically reversible phenomena, a single thermoelectric device may be operated as either a Seebeck temperature sensing element or a Peltier temperature cooling control element.

Temperature sensing elements disposed on- or off-platform may be comprised of one or more of a metal film thermistor, a semiconductor film thermister, bandgap diode, MOS transistor (MOST) and bipolar transistor. A temperature sensing element disposed on-platform may also be comprised of a Seebeck thermoelectric device.

Relating now to the analyte sensing element: Each analyte sensing element within the impedance sensor is coupled with an analyte through a resistive coupling or an electric, magnetic or electromagnetic field coupling. This coupling between the analyte sensing element and the analyte modulates a wired or wireless signal parameter which is received by the impedance analyzer and processed to provide a means of identification and monitoring of an exposed analyte.

The analyte sensing element may be comprised of one or more of an inductor L, a capacitor C, resistor R and antenna A or combinations thereof. The analyte sensing element is comprised of a nonresonant antenna or an LCR resonant antenna. The analyte sensing element is disposed on a micro-platform and may be physically configured, in embodiments, as a discrete L, C or R component or an LCR antenna. In other embodiments, a structured resistor R or capacitor C may have an overlay of nanotubes, graphene and/or films of other activation materials disposed thereon.

In some embodiments, the analyte sensor element is comprised of an interdigitated capacitor without any activation material. Applications of this embodiment include characterizing a particular analyte for freezing and boiling temperatures. In one application of this embodiment, wherein a freezing or frost temperature is determined, a dew point hygrometer is provided.

Relating to the activation material: In some embodiments, the analyte sensing element is comprised of activating material wherein either or both the real and imaginary components of its impedance change due to a chemical reaction or chemical doping process that occurs upon exposure to an analyte. The activating material increases the spectrometer sensitivity when exposed to an analyte of interest.

Activation materials are comprised of semiconductor and catalytic materials processed with and without a surrounding structural film. Activation materials include nanotubes of various materials, graphene, metaloxide compounds, metal oxides (MO) metal oxide frameworks (MOF), and organic charge donors (OCD) and organic acceptors (OCA) and noble metal catylists. The activating material, in embodiments, is suspended within a nanoparticle assembly (NPA) or colloidal crystal (CCMOF) or metal-organic framework (MOF). Activation materials comprising a semiconductor, the semiconductor may be doped to provide an initial electrical conductivity at a desired level. Synthesis for activation materials includes coevaporation, magnetron sputtering, chemical vapor deposition, and sol gel processes generally with multi-step thermal annealing and layering. These processes are well known to those skilled in the art.

In embodiments, the activating material may in itself provide a heater and thermistor function. In other embodiments, the activating material is a covering film including films disposed on a semiconductor or metal heater. Adhesion of a metallic activation film may be enhanced using an intermediate film of Cr or Ti. In many embodiments, the activating material is an ALD film. A chemi-resistive activation layer is used to enhance the sensitivity of a resistive-capacitive RC sensor element which is generally comprised of an underlying interdigitated capacitor or separated metal electrodes.

In sensor embodiments wherein the impedance sensing element is a MOST transistor or an MOS capacitor, the activation material is an ALD electron donor film disposed over the gate dielectric. A chemical reaction with the analyte deposits a charge on the gate dielectric and changes the flat band voltage of the MOST transistor or capacitor. MOST and MOS embodiments with an $SiO_2$ dielectric wherein the activation material is catalytically active Pt or Pd provide a sensor for hydrogen and unsaturated hydrocarbon analytes. In this embodiment, MOST and MOS sensors when operated over a temperature range provide unique impedance versus temperature responses which permit specific unsaturated hydrocarbons to be identified separately.

With activation materials comprised of polymers such as polyaniline, the imaginary component of a resistive component of an analyte sensor element changes when exposed directly to an acidic or basic vapor or liquid. Such activation polymers can be used, for example, to monitor the pH of HCl (acidic) and TMAH (basic) dilute vapors and microquantities of liquids.

An activation layer that binds to a ferromagnetic analyte such as compounds of iron, nickel and cobalt provide a modulated magnetic permeability modulating the inductance of an inductive analyte sensor element.

Activation materials comprising a semiconductor include $WO_3$, $TiO_2$, $ZnO_2$, $In_2O_3$, $CeO_2$, ZnO2, $MoS_2$, $In_2O_3$, CdS, $SnO_2$, PbS, $V_2O_3$, InSb, $In_xSn_yO_2$, graphene, nanotubes, semiconductor organic films and other organic films. In some embodiments, the activation material is organic film of donor type which deposits or diffuses charge into a sensor semiconductor or sensor dielectric. In embodiments, the activation material includes a catalyst comprising one or more of Pt, Pd, Ag, Au, Al, Cu, Fe, and Ni. These activation materials modulate the electrical impedance of the analyte sensor when exposed to an analyte.

In embodiments, selected activation materials provide for an impedance spectrometer sensitive to selected gas, vapor, solid or liquid analytes. The spectrometer is sensitive to gas and vapor analytes including one or more of analytes including, without limitation, $H_2$, $H_2C_2$, CO, $CO_2$, $NH_3$, $H_2S$, NO, $NO_2$, $BBr_3$, $SiH_4$, $CCl_4$, $H_2O_2$, $O_3$, HCl, humid air, organic compounds and mixtures. A gas or vapor analyte may be exposed to the impedance sensing element using a surrounding gas cavity collecting the analyte and with appropriate valves. A liquid analyte may be disposed onto the micro-platform using a micro-pipette and a micromanipulator. A solid analyte such as a tissue sample or cell culture may be positioned onto the micro-platform using a micro-manipulator. The heated micro-platform provides a means for ashing or evaporating analyte residue and, outgassing adsorbed analytes to provide a reset mechanism for the spectrometer.

Processing, packaging and assembly: In the exemplary embodiments of this invention, the starting wafer is a silicon sandwich structured as a semiconductor-on-insulator (SOI) wafer. The SOI wafer in these embodiments is comprised of a first semiconductor device layer of appropriate electrical conductivity, a sandwiched silicon dioxide film (BOX) of low electrical conductivity, and an underlying silicon handle substrate. The SOI starting wafer is typically manufactured by processes such as BESOI and SMARTCUT™. The SOI wafer is processed to provide a sensor using semiconductor manufacturing processes and processing tools including submicron optical and e-beam lithography, CVD, PVD, co-evaporation, magnetron sputtering, RTP, RIE, DRIE, annealing/diffusion furnaces and metrology familiar to those of ordinary skill in the art. Processing of the active silicon layer may include fabrication of integrated circuits, especially CMOS circuits, on or off the micro-platform. Final processing steps include release of the micro-platform using a backside or frontside etch and wafer dicing. Wafer handler cassettes designed to protect wafers with fragile micro-platforms are used as necessary.

To package the processed SOI wafer after it is processed at wafer scale, dicing techniques are used which do not damage the micro-platform and nanowire. For example, dicing can be performed using a $CO_2$ laser scribe operated to minimize ablation.

Silicon die are bonded on headers or other substrates by precision pick and place robotic tools or bonded using a manual placement micromanipulator. Die bonding is implemented with assembly processes that avoid damage to the micro-platform and support structure. In all embodiments the sensor die are packaged with headers that permit exposure to an analyte gas or vapor of interest. Ultrasonic wire bonding or solder bumps are used for connections within headers or onto circuit boards. In some embodiments, the analyte sensor element is enclosed within a window of porous material such as a microfilter that permits the analyte to readily diffuse or flow into the sensor wherein particulates are filtered out. The porous filter protects the analyte sensor element and micro-platform from damage due to unwanted particulates carried by the analyte.

Objectives: It is an object of the present invention to provide an impedance spectrometer comprised of an analyte sensing element disposed on a thermal micro-platform. It is an object of the present invention to provide an impedance spectrometer physically configured with phononic nanowires and to provide a sensor for identifying and monitoring gases, vapors, solids, and liquids as analytes exposed to a thermal micro-platform. It is an object of the present invention to provide, in embodiments, an impedance spectrometer comprised of a mobile phone. It is an object the present invention to provide an impedance spectrometer with increased miniaturization, sensitivity, accuracy, robustness, adaptability, reduced of power requirement, and stability of performance with manufacturability at reduced cost.

DETAIL DESCRIPTION

Definitions

The following terms as explicitly defined for use in this disclosure and the appended claims:

"impedance spectrometer" means an instrument for identifying, monitoring and characterizing an analyte based on determinations in the real and/or imaginary parts of the electrical impedance of an impedance sensing element exposed to the analyte.

"wired-type" and "wireless-type" mean an impedance spectrometer wherein the impedance analyzer and the impedance sensor communicate by wired and wireless means, respectively.

"thermal micro-platform" means a micro-platform supported by nanowires and wherein the nanowires provide a thermal isolation with respect to a surrounding support platform.

"phononic nanowire" means a wire of nanometer-scale cross section comprised of nano-dimensioned structure for scattering or resonating phonons providing a reduction in thermal conductivity.

"analyte" means a gas, vapor, solid or liquid exposed-to the analyte sensing element.

"analyte sensing element" means an impedance sensor element disposed on the micro-platform and exposed to an analyte "exposed" means resistive coupling or an electric, magnetic or electromagnetic field coupling between an impedance sensor element and an analyte.

"chemi-resistive sensor" means a sensor wherein the sensing function is based on a chemical reaction such as a catalytic reaction or doping and loading of a film including semiconductor, metal and polymeric films.

"chem-FET sensor" means a MOST transistor or MOS capacitive diode physically configured as an analyte sensing element.

"pellistor" means sensor device used to detect gases which are combustible by monitoring the temperature of a chemical reaction, generally the formation of water from hydrogen and oxygen in the presence of a catalyst.

"capnometer" means a sensor for measuring $CO_2$ in exhalation

"ALD" film means an atomic layer deposition film of thickness generally between 2 and 40 nm.

"disposed on" means a structure physically positioned on or created within. For instance, a resistive thermistor element disposed on a micro-platform may be physically bonded to the micro-platform or it may be created within the micro-platform.

Figure 1:
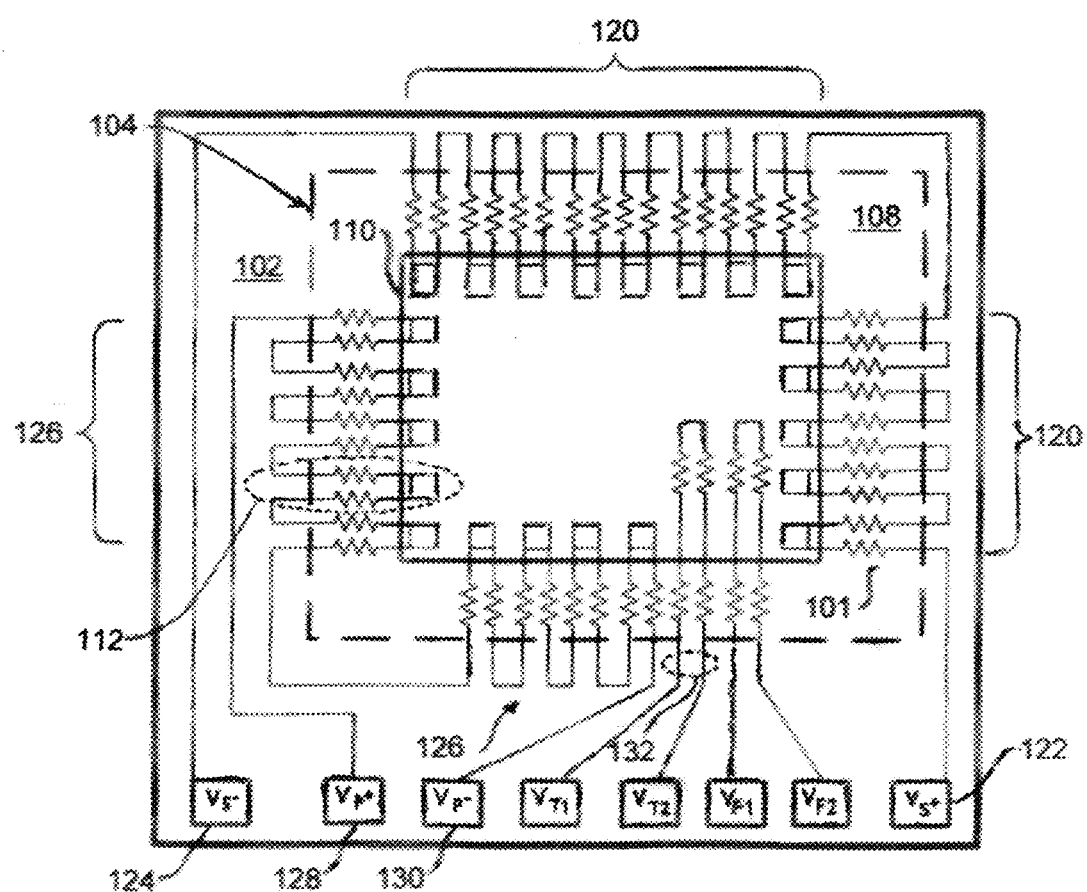
FIG. 1 depicts a plan view of a prior art micro-platform.

FIG. 1 depicts a plan view of a prior art thermoelectric sensor 100 disclosed in U.S. Pat. No. 9,236,552. The prior art sensor disclosed is comprised of a micro-platform 110 with supporting nanowires 101 disposed over a cavity 108 wherein the cavity is bounded by perimeter 104. The nanowires 101 attached to the micro-platform extend from a surround support platform 102. The pixel is comprised of thermoelectric elements 112 within a thermoelectric device 120. The resistor 132 depicts circuit connections and structures including thermistor resistors and integrated circuits disposed in or on the micro-platform 110. The series-connected array 120 of thermoelectric devices 112 is disposed around the periphery of the micro-platform 110 with connections through nanowires 101 to off-platform bonding pads 122 and 124. A second series-connected array 126 of thermoelectric devices 112 is disposed on the platform 110 with a connection through nanowires to bonding pads 128 and 130.

Figure 2A:
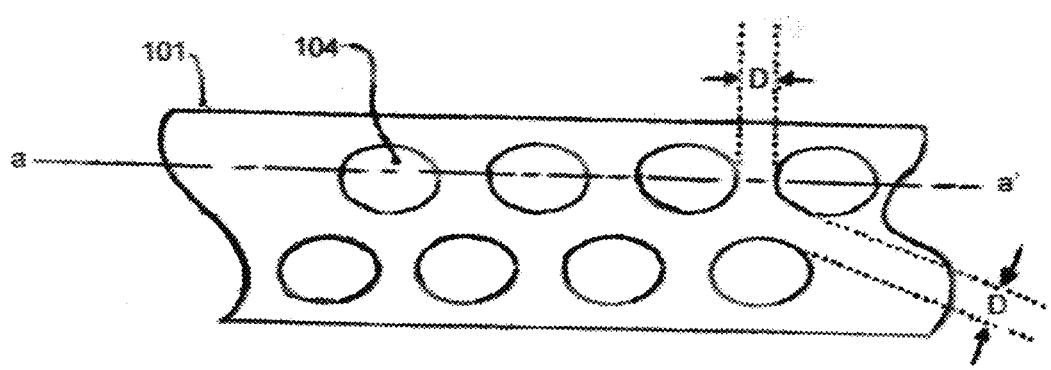
FIG. 2A depicts a plan view of a prior art nanowire with exemplary phononic structure.
Figure 2B:
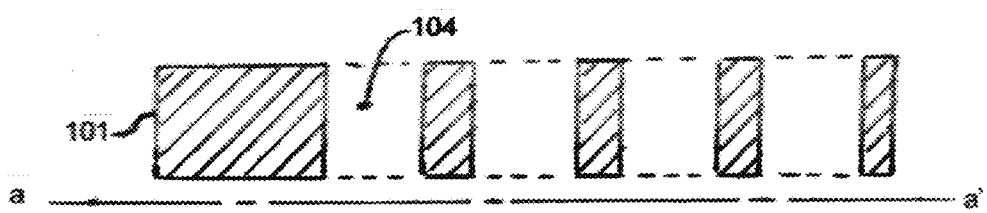
FIG. 2B depicts a cross-sectional view of a prior art nanowire with exemplary phononic structure.

FIG. 2A depicts an embodiment of prior art nanowires 101 with an exemplary phononic structural embodiment. In this embodiment, the phononic structures are comprised of holes 104 in the thin nanowire 101 film. The holes 104 are separated by a dimension D which is created to be less than the mean free path for phonons conducting heat along the length of the nanowire 101. FIG. 2B depicts a cross-sectional view of section a-a' of the FIG. 2A prior art nanowire 101 with exemplary phononic structural holes 104. The nanowire 101 is terminated on the micro-platform 110 and the surrounding support platform 102. The prior art phononic structuring of the pixel nanowire 101 reduces the thermal conductivity of the nanowire.

In embodiments, nanowires 101 are physically configured as patterned semiconductor nanofilms synthesized by depositions including evaporation, multi-source sputtering and sol-gel processes. These synthesis processes use appropriate precursors and specialized thermal annealing to form nanowires with mesoporous or clustered semiconductor phononic scattering structures comprised of one or more semiconductor materials.

In all embodiments, the thermal conductivity of the nanowire 101 is advantageously reduced by the physical phononic adaptation which has only limited effect on the electrical conductivity.

Figure 3:
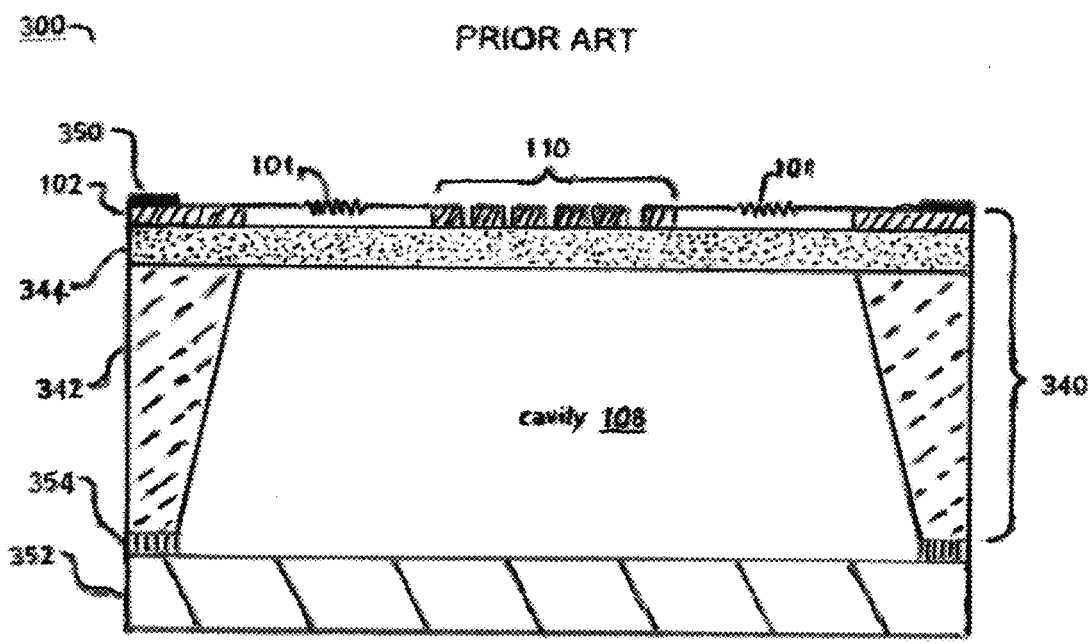
FIG. 3 depicts a cross-sectional view of a prior art micro-platform wherein supporting nanowires and underlying dielectric film are released with backside etching.
Figure 4:
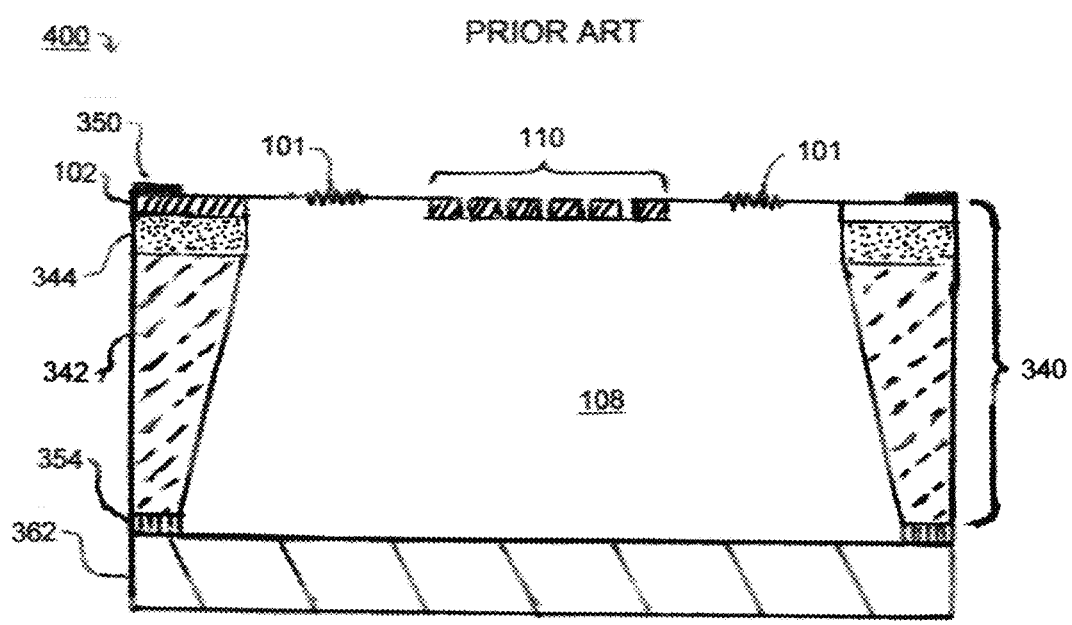
FIG. 4 depicts a cross-sectional view of a prior art micro-platform and phononic nanowires released with backside etching.
Figure 5:
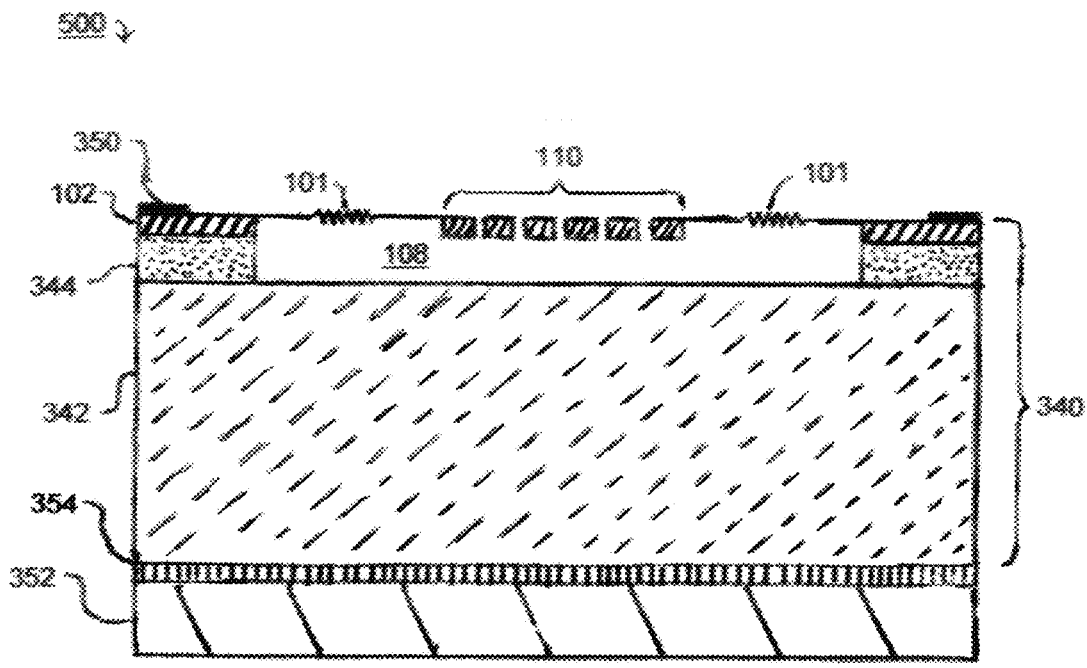
FIG. 5 depicts a cross sectional view of a prior art micro-platform and phononic nanowires released with frontside etch.

FIGS. 3, 4 and 5 each depict prior art cross-sectional views of the plan view of FIG. 1. These prior art examples are presented as fabricated from exemplary silicon wafers although in embodiments the starting wafers may comprise other starting wafers including semiconductors, ceramics and glass. The microstructure 340 comprising multiple patterned levels is generally formed from a starting semiconductor wafer. In these prior art embodiments dielectric layer 344 is generally comprised of silicon oxide, silicon nitride or aluminum oxide. The pixel includes micro-platform 110, nanowires 101, surrounding platform support 102 and the cavity 108 located under the micro-platform and nanowires. In the embodiment depicted in FIG. 3, a bottomside silicon etch releases the micro-platform 110 and nanowires 101 to form cavity 108. Backside etching is obtained with a plasma DRIE or with an anisotropic liquid etchant including TMAH, KOH, EDP or hydrazine wherein layer 344 an etch stop. A patterned metal film 350 such as Al or W—Ti provides the bonding pad area for external electrical connection through nanowires 101 to elements on the micro-platform 110. In these embodiments, topside structures above the cavity 108 are depicted as released from substrate 342 prior to die bonding. In assembly, the pixel is die bonded with adhesion layer 354 to external substrate 352. In these embodiments, platform and nanowire release processing is completed prior to wafer dicing and die bonding.

FIG. 4 depicts a cross-sectional view of a prior art micro platform 110 and support structures where the backside etch process is initially the same as for the FIG. 3 depiction but with an additional processing step. Backside etching creating the open backside cavity 108 is followed by a vapor HF etch which removes a portion of layer 344 from under the micro-platform 110 and nanowires 101.

FIG. 5 depicts a cross-sectional view of a prior art pixel structure using a topside release etch process. In SOI with a silicon dioxide BOX layer 344, the dielectric layer 344 is selectively removed from underneath the micro-platform 110 and the nanowires 101 to create cavity 108 using a vapor HF etchant. In this embodiment, topside structures are passivated against the vapor HF etch with a thin patterned protective film such as silicon nitride as appropriate.

Figure 6:
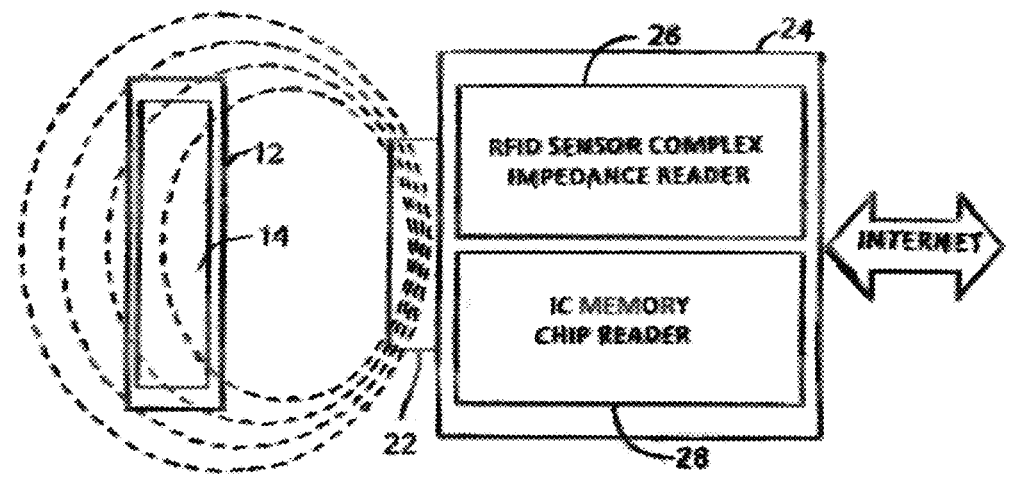
FIG. 6 is a schematic depiction of a prior art analyte sensing system with an electrical resonant circuit.

FIG. 6 is a schematic depiction of a prior art analyte sensor system 600 comprised of a wireless-type impedance reader. A system controller 24 comprised of an impedance reader 26 with antenna 22 and memory 28 is field-coupled by a magnetic field with an impedance sensor 12. The impedance sensor is closely coupled with the analyte 14 and operates typically at 13.56 MHz. Prior art does not disclose an impedance spectrometer comprised of a thermal microplatform with supporting nanowires wherein the nanowires are comprised of phononic structures.

Figure 7A:
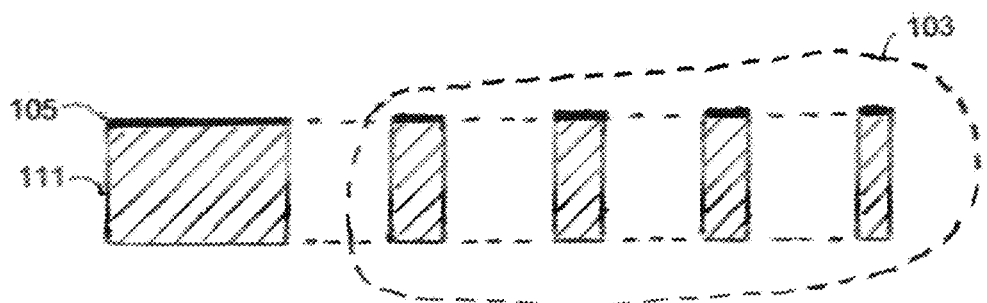
FIGS. 7A, 7B and 7C depict cross-sectional views of a nanowire comprised of two, three and four structural thin films in accordance with the present teachings.
Figure 7B:
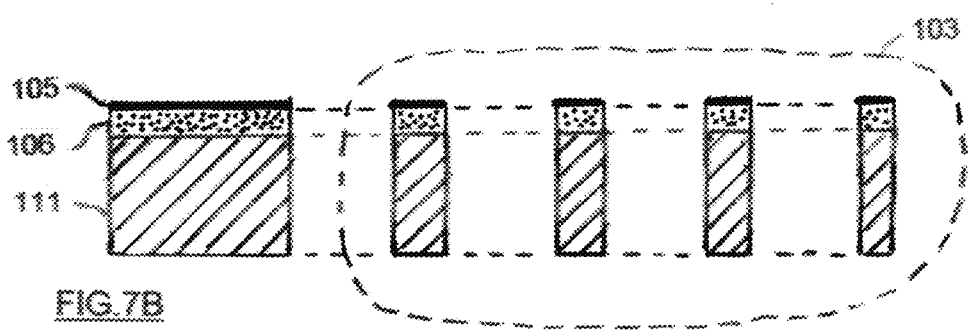
Figure 7C:
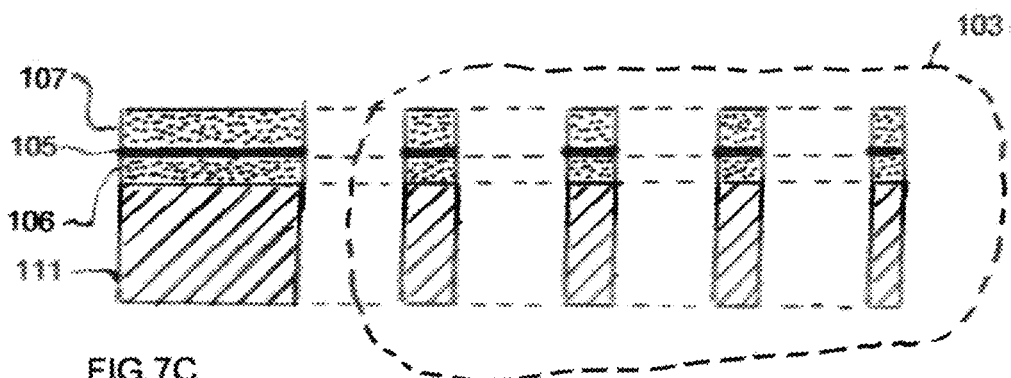

FIGS. 7A, 7B and 7C depict the cross-section of nanowire 101 physically configured with additional topside layers of metal and dielectric films as nanowire 103. These FIGS also show the exemplary nanowires attached to a portion of the surrounding support platform 111. FIG. 7A depicts the nanowire 103 and surrounding support area 111 formed from the device layer of a starting wafer and with an overlying metal layer 105. In embodiments, the metal layer increases the electrical conductivity of the nanowire and is created by sputtering or evaporative deposition to provide a film, generally an ALD film. FIG. 7B depicts a nanowire 103 and surrounding support area 111 physically configured with a dielectric layer 106 sandwiched between an overlying metal film 105 and the device layer of the starting wafer. The dielectric layers in some embodiments include $Si_3N_4$ obtained by a CVD process using $NH_3$ and $SiH_4$ as precursors. In another embodiment, the dielectric layer 106 is $SiO_2$ obtained by using a oxide target with RF sputtering. In other embodiments, the dielectric layer 106 is a film of $Al_2O_3$. FIG. 7C depicts the nanowire 103 and surrounding support area 111 structurally configured with an additional overlying dielectric film 107. In embodiments, the dielectric films 106 and 107 provide passivation against one or more of process etch species, electrical insulation and stress.

Figure 8:
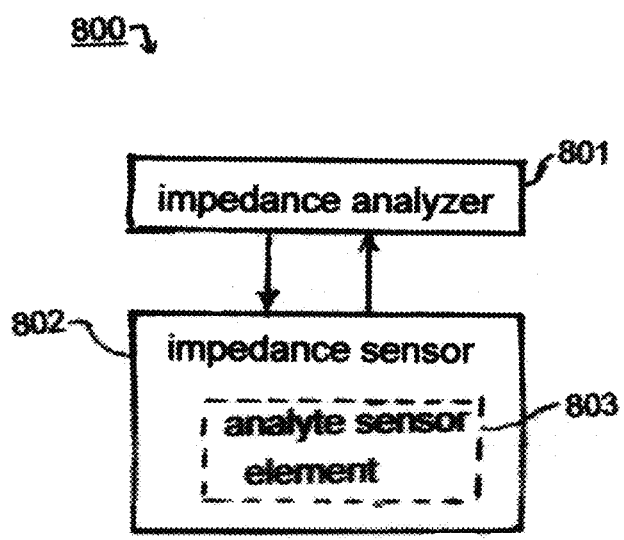
FIG. 8 is a schematic depiction of the impedance spectrometer having a wired means of readout in accordance with the present teachings.

FIG. 8 is a schematic depiction of a wired-type of impedance spectrometer with a wired means of communication and readout from the impedance sensor 802 in accordance with the present teachings. This schematic depicts an impedance analyzer 801 with a wired connection to the impedance sensor 802 which further comprises an analyte sensor element 803. The analyte sensor element 803 is comprised of one or more of inductive L, capacitive C, and resistive R elements including resonant and nonresonant combinations thereof.

FIGS. 9 through 13 depict analyte sensor elements 803 which may be disposed within a wired-type impedance spectrometer 800. These same analyte sensor elements may also be disposed within more complex impedance sensor embodiments to provide a wireless-type impedance spectrometer 1400. An example of a more complex wired impedance sensor embodiment is the sensor comprised of a local memory unit separate from the impedance analyzer.

Figure 9:
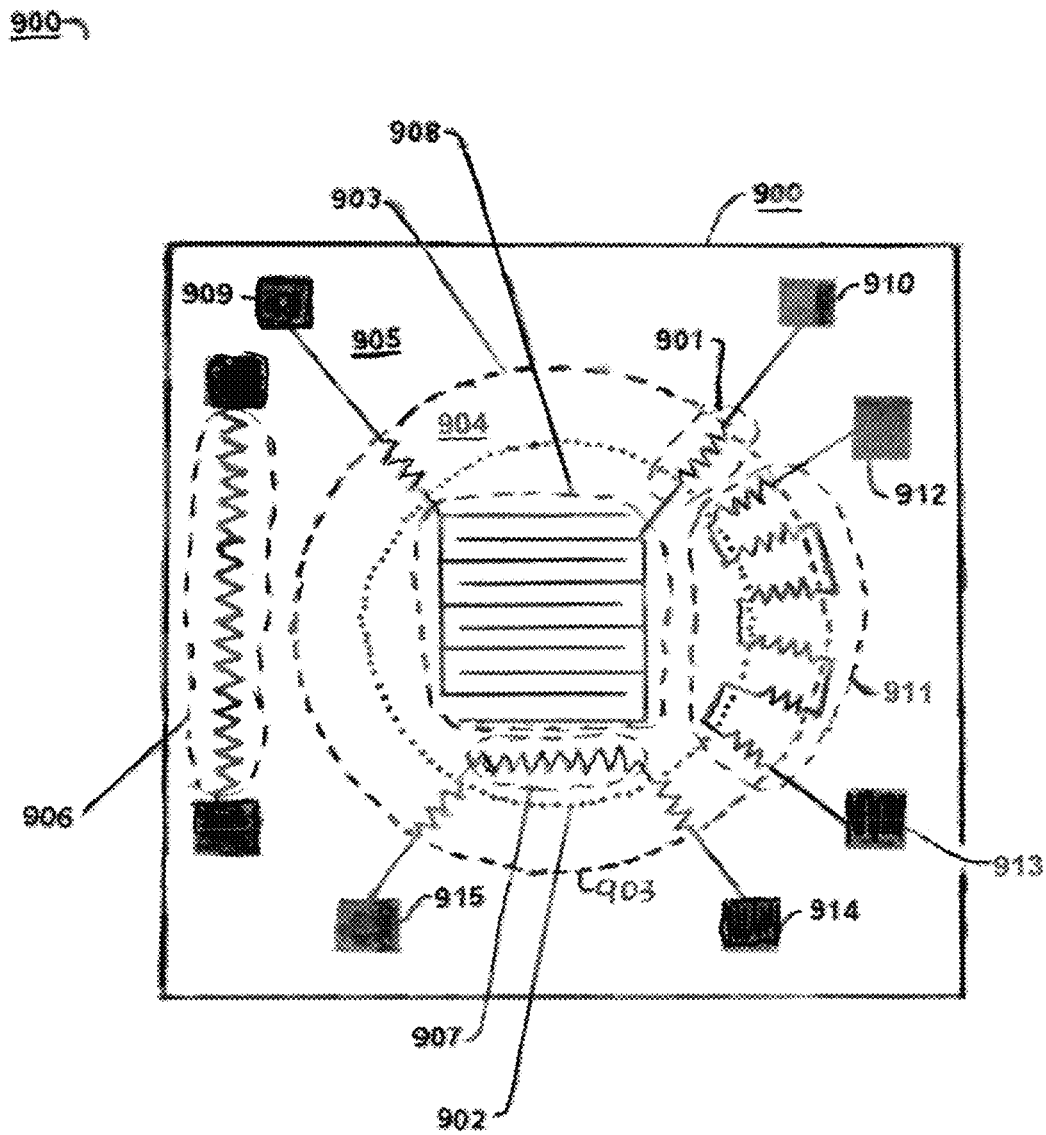
FIG. 9 depicts a plan view of an impedance sensor chip having a micro-platform comprised of a resistive sensor element, an on-platform thermoelectric element and with on- and off-platform thermistors in accordance with the present teachings.

FIG. 9 depicts a plan view of an impedance sensor 900 embodiment having a micro-platform 902 comprised of a sensing element comprised of interdigitated electrodes 908, capacitive sensor element 908, an on-platform thermoelectric device 911 and an on-platform thermistor 907. In this embodiment, a single semiconductor chip comprises the impedance sensor 900. The starting wafer is silicon SOI with an n-type device layer. The micro-platform 902 is supported by nanowires 901 are formed of the silicon device layer and released over cavity 904 within cavity perimeter 903. The off-platform thermistor 906 is connected with contact pads 906 and 908. The on-platform thermistor 907 is connected with contact pads 914 and 915. The thermoelectric device 911 is connected with bonding pads 912 and 913. The analyte sensing element is comprised of the interdigitated capacitor 908 which is connected with bonding pads 909 and 910. In embodiments, the thermoelectric device 911 provides a precision temperature sensor or a platform cooler. An off-platform thermistor 906 provides a reference temperature for the surrounding support platform 905. All contact pads of the impedance sensor 900 are wired to respective connections on the impedance analyzer 801. All functions provided by the impedance sensor 900 are monitored and controlled from the impedance analyzer 801. In this embodiment, the resistive sensors 906 and 907 are formed from an n-type device layer with a patterned boron diffusion. The thermoelectric nanowires 911 are also created from the device layer by heavy doping of appropriate p-type and n-type dopants. In embodiments, the nanowire connections to bonding pads are electrically isolated from the surrounding support platform 905.

The capacitive reactance of interdigitated structurer 908 has its electrical impedance modulated by field coupling with the exposed analyte. This coupling affects both the real and imaginary parts of the impedance of sensor element 908. In general, the real part $\epsilon'$ of the analyte bulk permittivity primarily modulates the imaginary part of the sensor impedance. The real part ε' of the analyte bulk permittivity primarily modulates the imaginary part of the sensor impedance. In embodiments, the interdigitated sensor element may be operated to characterize a known analyte for a physical or chemical parameter such as threshold temperature for a chemical reaction. The impedance analyzer determines one or more components of the capacitor impedance as datapoints and matches these measured datapoints to stored calibrations using analysis programs to provide an identification and monitoring of the analyte.

The impedance sensor 802 of FIG. 9 can, in embodiments, be operated to determine a physical characteristic of a known or unknown analyte. In an embodiment, the interdigitated sensor is operated to provide an absolute dew point hygrometer. When the micro-platform 902 is cooled to a dew point or frost point temperature by thermoelectric cooler 911, condensation of liquid or the formation of ice across the interdigitated electrodes causes an increase in the electrical capacitance of the sensor element 908. In this embodiment, the isothermal micro-platform is cooled by thermoelectric device 911 operated as a Peltier cooler. Platform temperature is monitored by thermistor 907. The electrical impedance of the analyte sensor element 908 is monitored by the impedance analyzer 801 to determine the critical dew point or frost point temperature of the analyte. The impedance analyzer 801 uses this critical temperature datapoint together with calibration lookup tables and appropriate algorithms to determine the humidity level of a gas or vapor analyte.

Figure 10A:
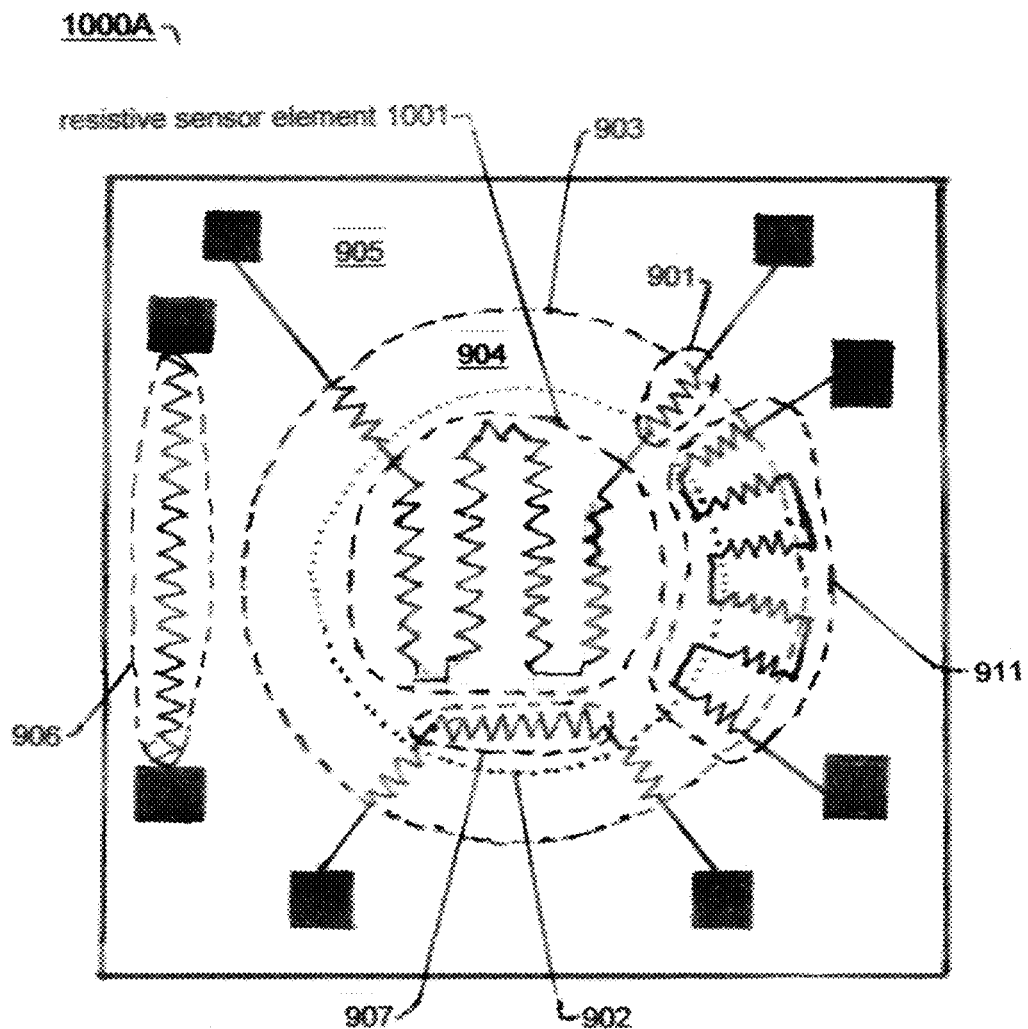
FIG. 10A depicts a plan view of an impedance sensor chip having a micro-platform comprised of a resistive sensor element, an on-platform thermoelectric element and with on- and off platform thermistors accordance with the present teachings.

FIG. 10A depicts a plan view of an impedance sensor 1000A chip comprised of a resistive sensor 803 operated within an impedance spectrometer 800. The impedance sensor 1000A is connected by wires to the impedance analyzer 801. The impedance sensor 1000A is physically configured with a circular micro-platform 902 released over cavity 904 bounded by periphery 903. The micro-platform 902 is supported by nanowires 901 partially disposed on surrounding support platform 905. The micro-platform 902 is comprised of resistive sensing element 1001 exposed to the analyte, a first thermistor sensor 907 and thermoelectric device 911. In this embodiment, the thermoelectric device 911 is operated as a Seebeck temperature sensor with increased precision and sensitivity. The thermoelectric device 911 is operated as a Peltier cooler in other embodiments. The electrical contact pads of the impedance sensor 1000A are connected by wire to the impedance analyzer 801. In embodiments, the resistor element 1001 is comprised of a diffused region created within the device layer of a starting SOI wafer with at least one overlying ALD film of activating material. In other embodiments, the sensing element 1001 is comprised of a sandwich comprised of an ALD metal heater and an activation material disposed over a dielectric insulating film. The first thermistor 907 may also be operated as a heater for the micro-platform 902.

FIG. 1000B depicts another resistive impedance sensor 1000B chip with a link to impedance analyzer 801. In this embodiment, the analyte sensing element 1003 and a first reference thermistor sensing element 1004 are comprised of separate thermally isolated micro-platforms. The sensing element 1003 and reference element 1004 are thermally isolated with nanowires 901 and disposed over cavity 904. The analyte sensing element 1003 and the first reference thermistor element 1004 are of the same physical size and are both formed from the patterned device layer 1005 of the starting SOI wafer.

In embodiments with the sensor chip 1000B, the two micro-platforms 1003 and 1004 are released using a topside etch. Portions of the silicon dioxide BOX layer of the starting SOI wafer are partially protected by a patterned $Si_3N_4$ film. In embodiments, the sensing element 1003 is activated with an ALD semiconductor film having an appropriate adhesion ALD adhesion film.

In this embodiment with two resistive elements, the difference in the real part of the electrical impedance is determined. This differential in electrical resistance is measured typically using one or both a Wheatstone bridge circuit and a potentiostat circuit. This differential is measured and processed to provide identification and monitoring of the exposed analyte.

Figure 10B:
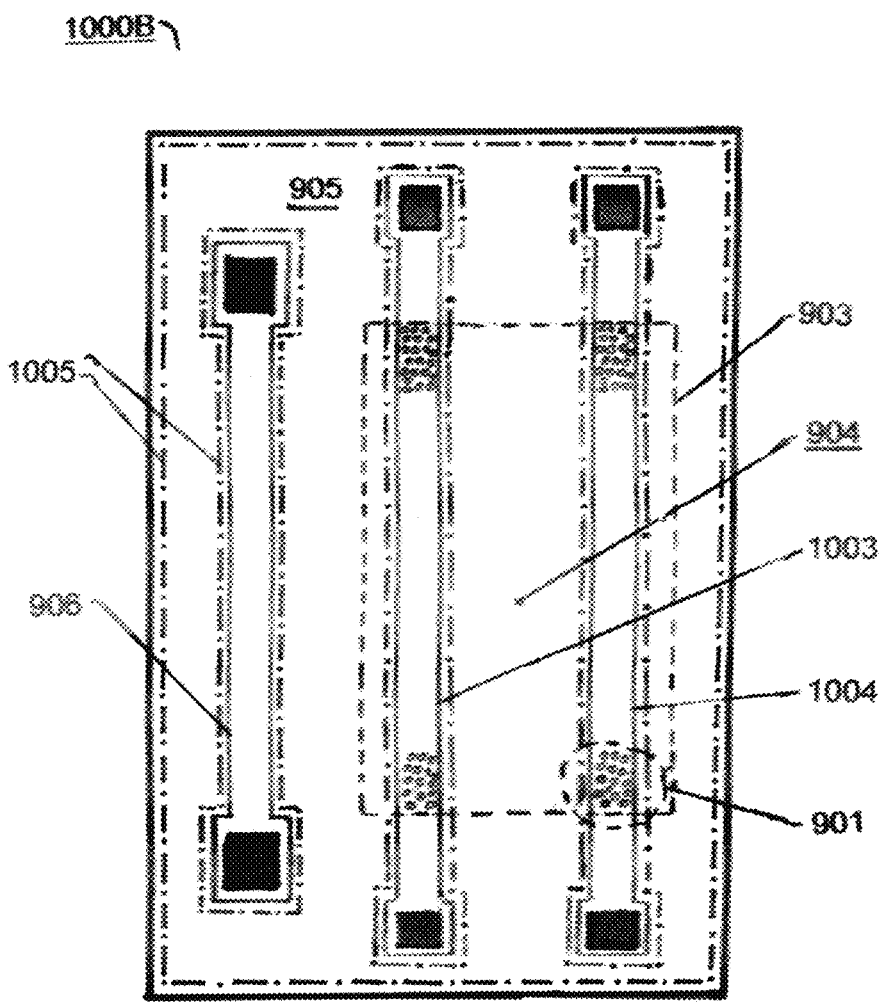
FIG. 10B depicts a plan view of an impedance sensor chip with a resistive sensor, an on-platform thermister and an off-platform thermistor.

In a specific embodiment using the sensor of FIG. 10B, a capnometer application, the resistive sensor element is activated with an ALD film of ZnO(La) to provide a chemi-resistive sensor within the impedance spectrometer wherein the electrical conductance of the resistive sensor changes when exposed to the $CO_2$ component of expired breath.

In all embodiments of FIG. 10A and FIG. 10B, the impedance sensor element 1001 is exposed to an analyte of interest. The connected impedance analyzer 801 is operated to determine the electrical resistive component of the impedance of the sensing element 1001 at precise temperatures for the purpose of identifying and monitoring the analyte.

Figure 11:
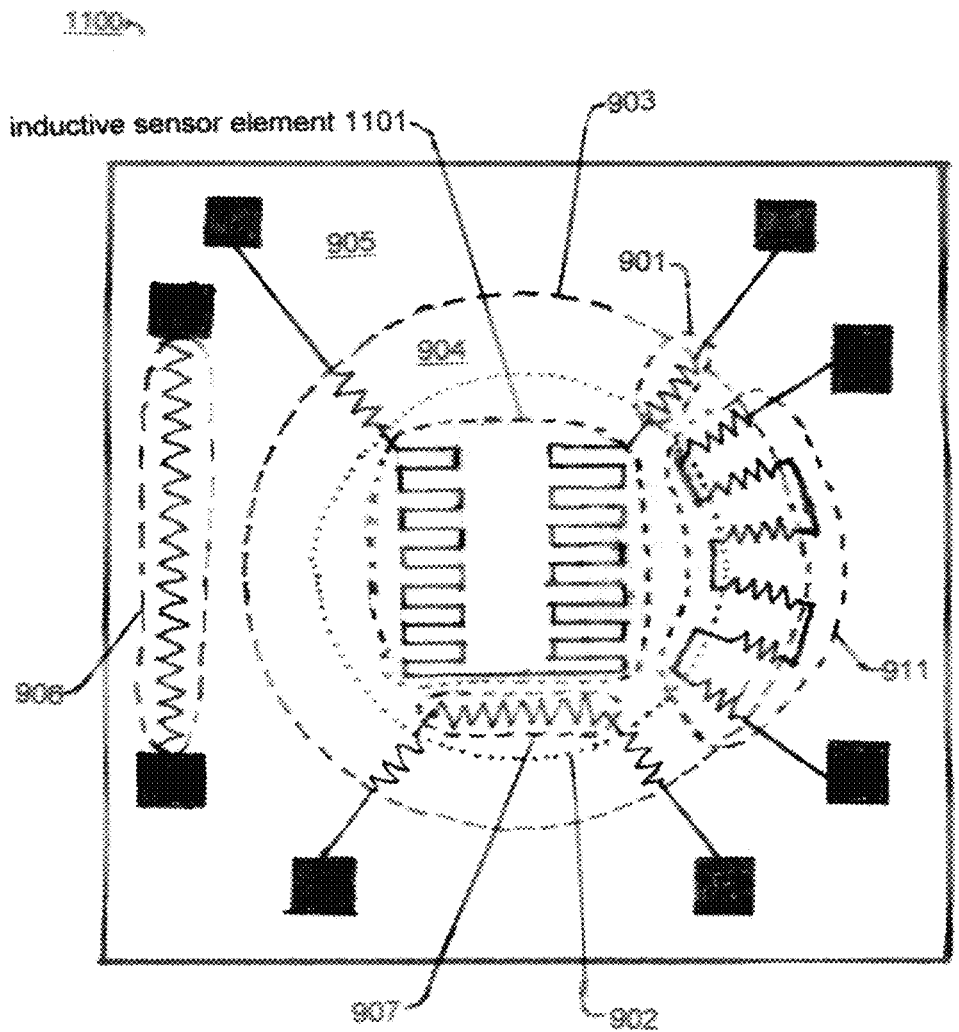
FIG. 11 depicts an impedance sensor chip comprised of a micro-platform comprising an inductive sensor element, a thermoelectric element and with on- and off-platform thermisters in accordance with the present teachings

FIG. 11 depicts the plan view of an impedance sensor 1100 chip physically configured with a circular micro-platform 902 comprised of an inductive sensor element 1101, a thermoelectric device 911 and an on-platform thermistor 907 in accordance with the present teachings. An off-platform thermistor 906 provides a reference temperature for the surrounding support structure 905. In this embodiment the sensor element is inductive and provides a sensitivity to the magnetic permeability of an analyte. The permeability of the analyte modulates the impedance of the impedance sensor when interrogated at high frequency thereby providing a means of analyte identification and monitoring. This embodiment is sensitive to analytes with magnetic properties such as compounds of iron and nickel. In general, the inductive sensor is used with micron-size solid and liquid analytes.

Figure 12:
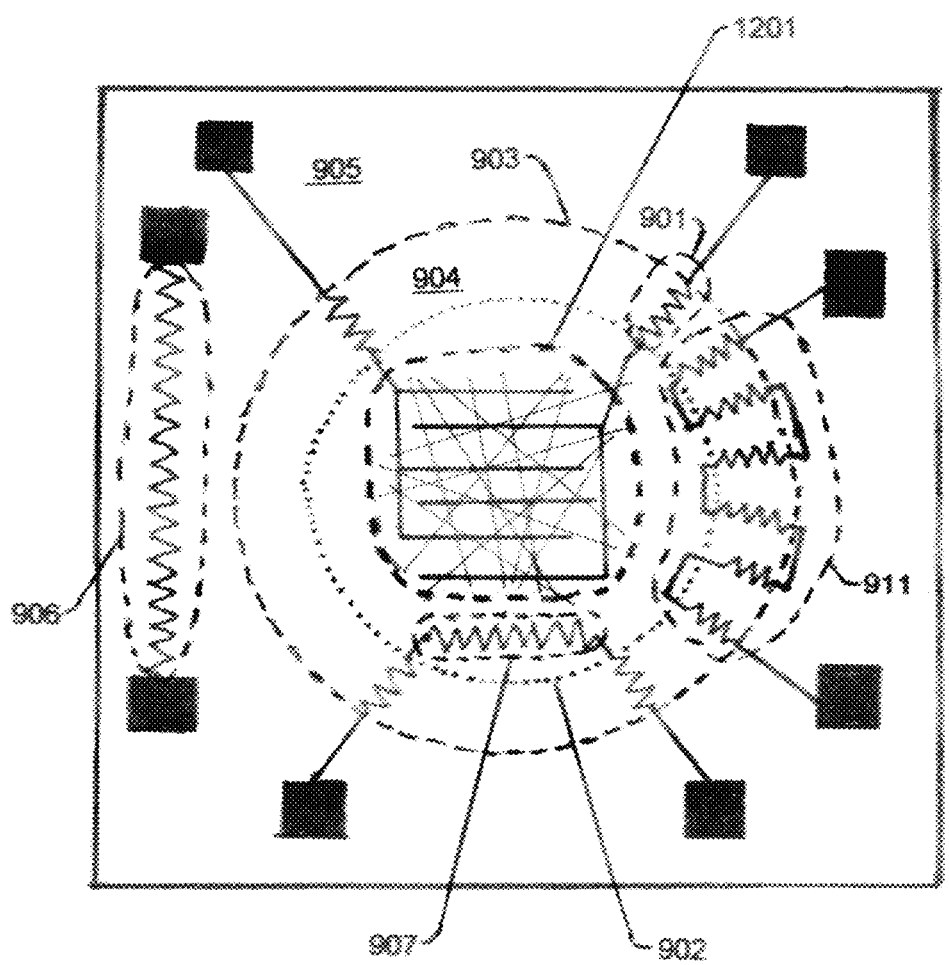
FIG. 12 depicts an impedance sensor chip comprised of a micro-platform comprised of a resistive-capacitive sensor, a thermoelectric device and with on- and off-platform thermisters in accordance with the present teachings.

FIG. 12 depicts an RC impedance sensor 1200 chip within an impedance spectrometer 800. The sensor is physically configured with a circular micro-platform 902 comprising a resistive-capacitive RC analyte sensor element 1201, a thermoelectric device 911 and an on-platform thermistor 907 in accordance with the present teachings. In a preferred embodiment, the interdigitated RC sensor element 1201 is disposed on the micro-platform 902 and processed to obtain an overlay of graphene or nanotubes. The micro-platform 902 is disposed over cavity 904 within periphery 903. An off-platform thermistor 906 provides a reference temperature for the surrounding support structure. In this embodiment the analyte sensor element 1201 is comprised of an interdigitated capacitor and electrodes with a parallel circuit comprising graphene or nanotubes. In embodiments, the graphene or nanotubes are activated further with a material to enhance response to the analyte. In embodiments, the overlay may comprise films without the graphene or nanotubes such as doped polymers sensitive to an analyte. The analyte modulates the impedance of the analyte sensor element providing a means for analyte identification and monitoring.

Figure 13:
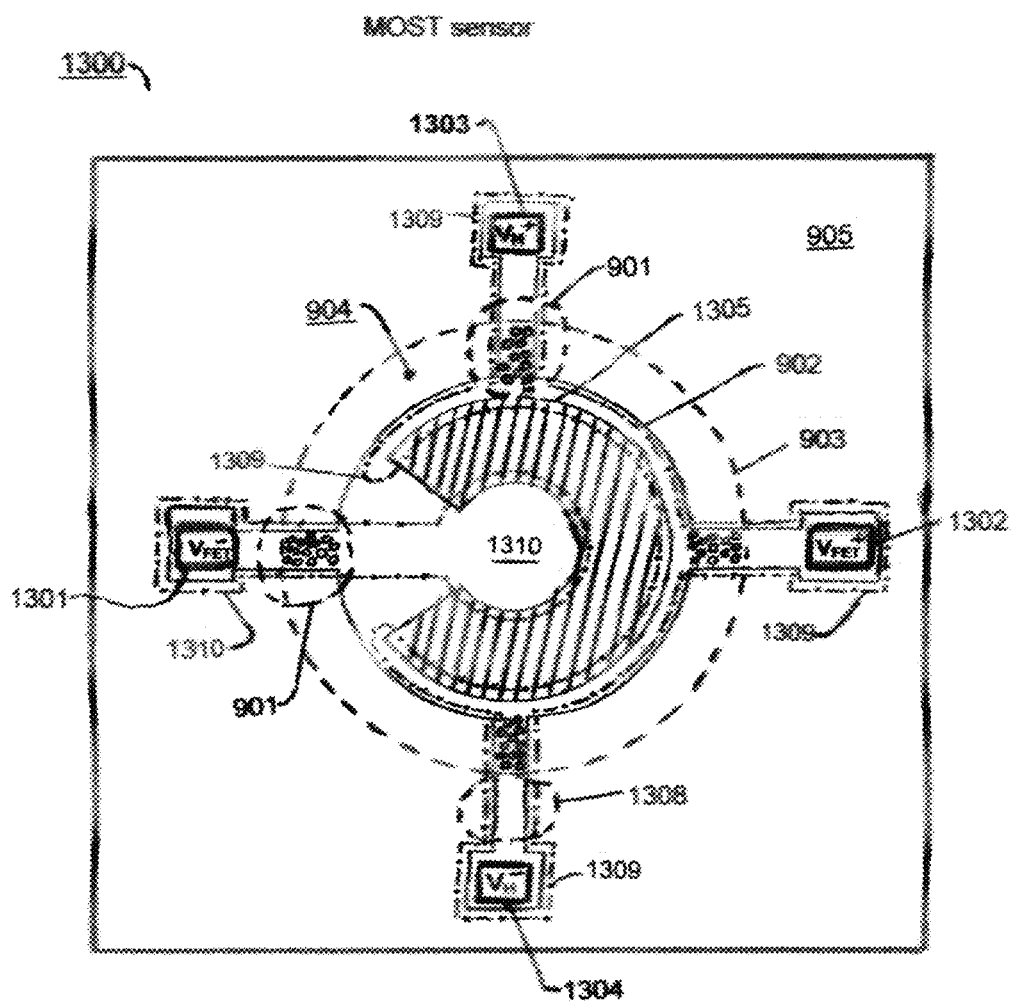
FIG. 13 depicts an impedance sensor chip having a micro-platform comprised of a MOST transistor sensing element in accordance with the present teachings.

FIG. 13 depicts an MOS impedance sensor 1300 with a circular micro-platform 902 physically configured in a circular format and comprised of a MOST transistor sensing element with electrical contacts 1301 and 1302. The micro-platform 902 in this embodiment is comprised of an MOST transistor processed using standard CMOS production processing. The micro-platform 902 is supported by nanowires 901 with extended connection traces 1308. A diffused resistor 1309 provides both a heater and thermistor disposed on the micro-platform 902 with bonding pad connections 1303 and 1304. The MOST transistor is sensed through bonding pads 1301 and 1302 using a preamp with differential input. The diffused heavily doped resistive region 1309 also provides the source of the MOST transistor. Diffusion area 1310 provides the drain of the MOST transistor. Dielectric 1305 overlapping both the source 1309 and drain 1310 provides a floating gate for the MOST transistor. The turn-on voltage $V_T$ for the MOST transistor is set with ion implantation and appropriate annealing processing.

An ALD activation film is disposed on the MOS gate dielectric 1305. This ALD film when exposed to an analyte receives an electric charge from a donor reaction in the ALD film. The resulting charge is retained on the ALD film or diffuses into the gate dielectric thereby changing the threshold voltage $V_T$ of the MOST transistor. In applications, an analyte is exposed directly to the gate 1305 where adsorbed gas or vapor species create a surface or trapped charge thereby modulating the electrical transconductance of the MOS channel. The primary means of transduction in this embodiment is deposition of charge from the analyte.

The MOS embodiment benefits substantially from a heated micro-platform because some charging mechanisms are accelerated at elevated temperature providing a faster response to an exposed analyte. In other embodiments, operated at elevated temperature, the charge stored within the gate dielectric undergoes a recombination process to "reset" the MOST transistor baseline transconductance to an reference level.

Figure 14:
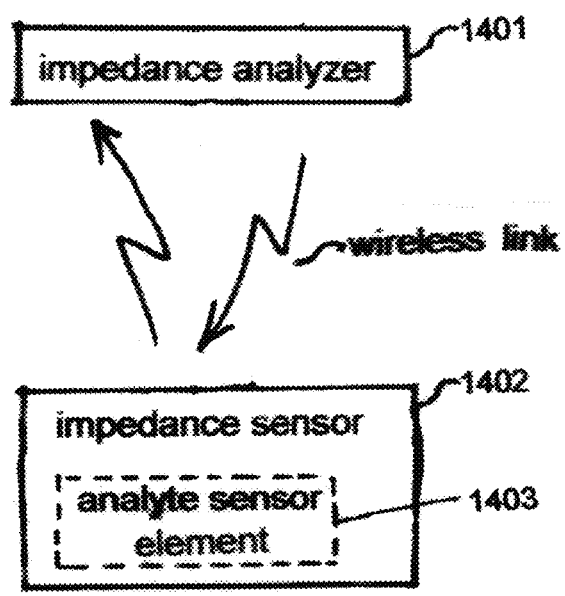
FIG. 14 is a schematic depicting an impedance spectrometer having a means of wireless readout in accordance with the present teachings.

Spectrometer with a wireless link: FIG. 14 is a schematic depicting a wireless-type impedance spectrometer 1400. In this embodiment, the impedance analyzer 1401 interrogates the impedance sensor 1402 over a wireless link which is comprised of an electric, magnetic or electromagnetic field-coupling. The impedance sensor 1402 comprises an analyte sensor element 1403 which is further resistive-coupled or field-coupled with an analyte. FIG. 14 depicting a wireless-type spectrometer embodiment is complementary to FIG. 8 which depicts a wired-type spectrometer embodiment.

Figure 15A:
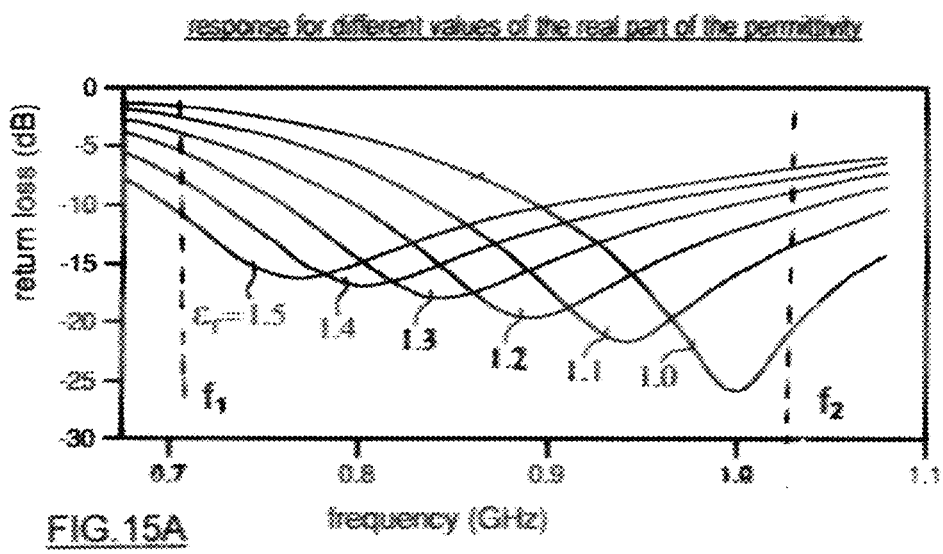
FIG. 15A is a graph presenting a simulation depicting response of a resonant sensing element for different values of the real part of analyte bulk permittivity

FIG. 15A is a simulation graph depicting response of a resonant LCR impedance sensor 802 or 1402 with field-coupling provided by the analyte sensor element 803 or 1403 and plotted for multiple values of the real part of bulk permittivity $\varepsilon'$ wherein the bulk permittivity is expressed as $\varepsilon = \varepsilon' - \varepsilon''$. In this simulation, the imaginary part $\varepsilon''$ of analyte permittivity $\varepsilon = \varepsilon_r - j\varepsilon''$ is held constant throughout. The graph of FIG. 15A shows return loss $S_{11}$ which corresponds to a signal amplitude provided by the impedance sensor 802 or 1402 as a function of sensing frequency. When the impedance sensor is interrogated at a frequency such as $f_1$ and $f_2$ removed from a resonant frequency $f_o$, the return loss response $S_{11}$ is a smoothly changing function of the real part of analyte permittivity $\varepsilon_r$.

Figure 15B:
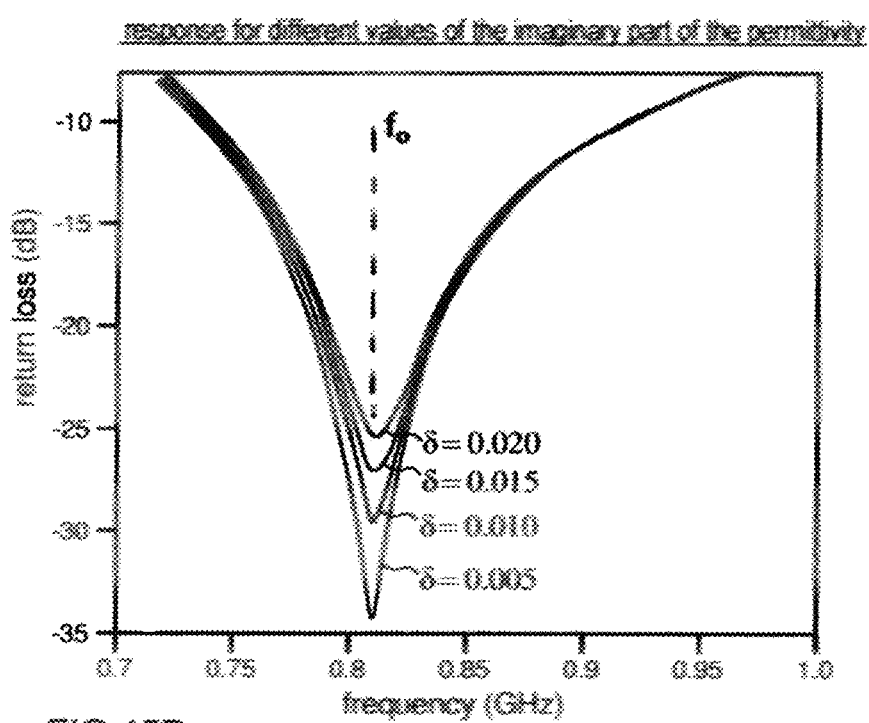
FIG. 15B is a graph presenting a simulation depicting response of a resonant sensing element for different values of the imaginary part of bulk analyte permittivity.

FIG. 15B is a graph presenting a simulation depicting response of a resonant impedance sensor 802 or 1402 for different values of the loss tangent $\delta = \varepsilon''/\varepsilon_r$ and with the real part $\varepsilon_r$ held constant throughout. At the resonant frequency $f_o$ point of minimum return loss, the return loss $S_{11}$ is a smoothly changing function of the loss tangent $\delta$ of the analyte bulk impedance.

A first sensing method embodiment is understood by inspection of FIGS. 15A and 15B. In this method embodiment, the analyte sensor element is interrogated with multiple frequencies by the impedance analyzer. In this first embodiment method, the impedance analyzer obtains $S_{11}$ signal by scanning with its frequency $f_a$ over a frequency range to determine the primary resonance frequency $f_o$ with an exposed analyte. The measured signal amplitude $S_{11}$ at $f_o$ provides a unique value for the loss tangent $\delta = \varepsilon''/\varepsilon_r$ based on calibrations of the impedance spectrometer with the analyte. Next, the $S_{11}$ signal amplitude obtained at a frequency $f_1$ or $f_2$ significantly removed from with calibration provides a unique value for the real part of bulk permittivity $\varepsilon_r$.

It is clear from FIG. 15B that the $S_{11}$ signal response at frequencies $f_1$ and $f_2$ removed from the primary sensor resonance frequency $f_o$ are independent of loss tangent $\delta$. Therefore, $S_{11}$ readings obtained with frequencies $f_1$ or $f_2$ uniquely determine the real part of the analyte bulk permittivity. This method comprising measurements with the impedance analyzer scanning over a range of frequencies $f_a$ provides a unique determination of the real $\varepsilon_r$ and imaginary $\varepsilon''$ values of bulk permittivity for an analyte of interest based on spectrometer calibrations. This method of determining the complex bulk permittivity of an analyte with calibrations correlates directly with and provides a means of identifying and monitoring a specific analyte special of interest. The example simulations of FIGS. 15A and 15B showing $S_{11}$ signal magnitudes as a function of frequency are representative of the range of signal amplitudes available from an analyte sensor element which in embodiments may be also used to identify and monitor an analyte.

In a second sensing method embodiment, the impedance sensor is comprised of a circuit which provides a means for tuning the primary resonant frequency $f_o$ of the analyzer sensor element to match a fixed interrogation frequency $f_a$ from the impedance analyzer. In this embodiment the interrogation frequency of the impedance analyzer $f_a$ is fixed. In this embodiment, a first tuning of the analyte sensor element tunes the exposed sensor element to a first resonant frequency $f_{o1}$ which is the same as that of the impedance analyzer frequency $f_a$ to obtain $f_{o1} = f_a$. Measurement of the $S_{11}$ signal amplitude with $f_{o1} = f_a$ uniquely determine the loss tangent $\delta$ of the analyte using calibration data previously acquired. Next, the analyte sensor element is tuned to a frequency $f_s = f_1$ or $f_2$ removed from the analyzer interrogation frequency $f_a$ to determine the real part $\varepsilon_r$ of the analyte permittivity. This alternate identification method requires an analyte sensing element which can be tuned. This second embodiment is useful for impedance spectrometers wherein the impedance analyzer is comprised of an RFID interrogator reader and the analyzer frequency $f_a$ is available only for a very limited frequency range.

An exemplary transponder circuit with capability for tuning an analyte sensing element applicable to the present invention disclosed in U.S. Patent Application 2017/0237466 which is included by reference in this disclosure.

Increased precision and accuracy for identification and monitoring of an analyte using a resonant LCR analyte sensor element is obtained when the impedance analyzer interrogates the impedance sensor 802 or 1402 with multiple temperatures, additional frequencies and over a time period to include transient responses.

The method based on the simulations of FIGS. 15A and 15B for identifying and monitoring an analyte using a resonant analyte sensor element measuring an $S_{11}$ signal level is applicable to both the wired-type and wireless-type of impedance spectrometer.

Figure 16:
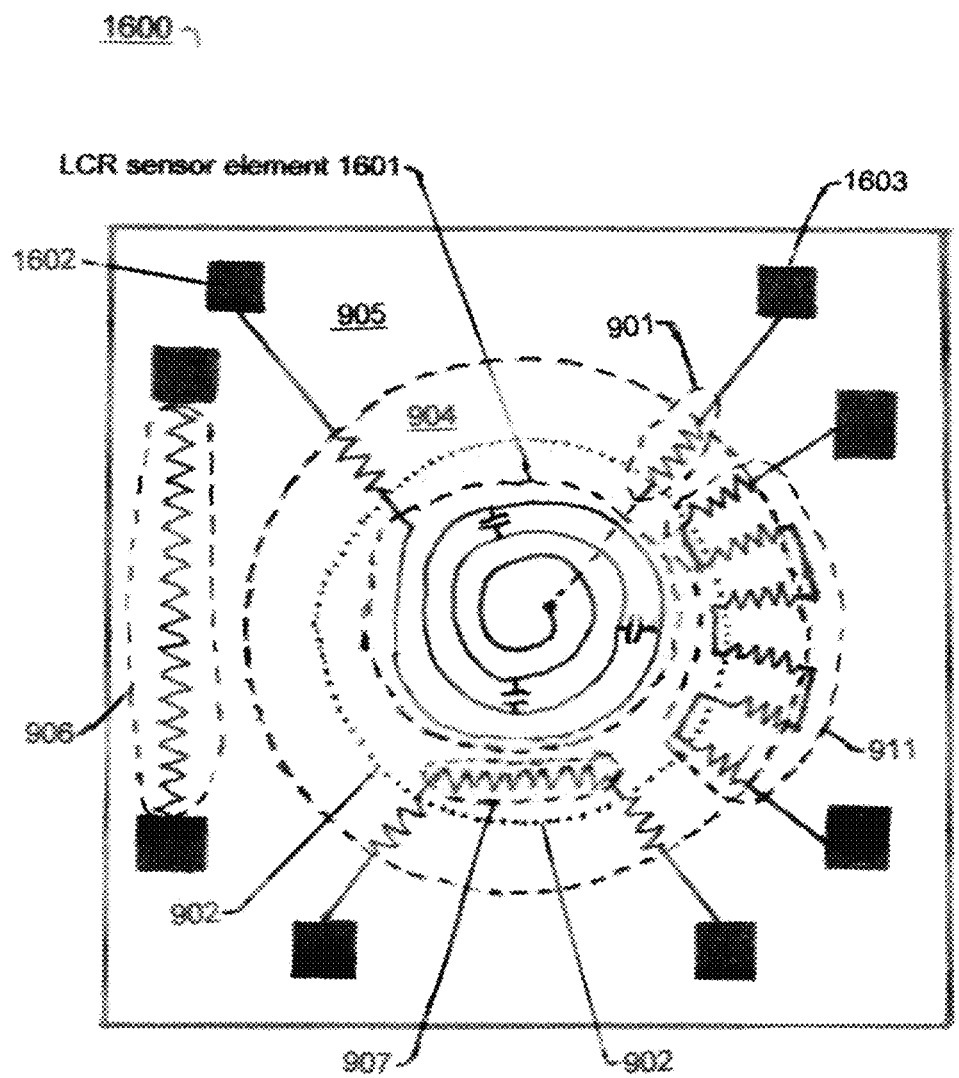
FIG. 16 depicts an impedance sensor element chip having a micro-platform comprised of a resonant LCR antenna, a thermistor and a thermoelectric device in accordance with the present teachings.

FIG. 16 depicts an impedance sensor component disposed on a chip 1600 physically configured with a circular micro-platform 902 comprised of an analyte impedance sensor element 1601, an on-platform thermistor 907 and a thermoelectric device 911. An off-platform thermistor 906 provides a reference temperature sensor for the surrounding support platform 905. The micro-platform 902 is disposed over cavity 904. The thermoelectric device 911 can be operated as either a precision temperature sensor or a Peltier cooler.

In an embodiment with the impedance sensor chip 1600, the LCR sensor element 1601 having contact pads 1602 and 1603 shorted together provides a complete impedance sensor within a wired-type impedance spectrometer. In this embodiment, the sensing sensitivity of element 1601 may be enhanced by an overlay of graphene, nanotubes, and additional activation material. For example, an analyte sensor element 1601 comprised of single wall nanotubes has enhanced impedance sensitivity to volatile organic chemicals (VOCs) when further activated with a polymer such as polythiophene and HFIP.

In another embodiment, the LCR sensor element 1601 provides both an analyte sensor element 1403 and an antenna function within a more complex impedance sensor 1402. In this embodiment, for example, the analyte sensor element 1600 is disposed together with a circuit which tunes the antenna 1601 under program control from the impedance analyzer. This embodiment expands the spectrometer capability wherein the impedance analyzer is an RFID interrogator operating over a limited frequency range.

Figure 17:
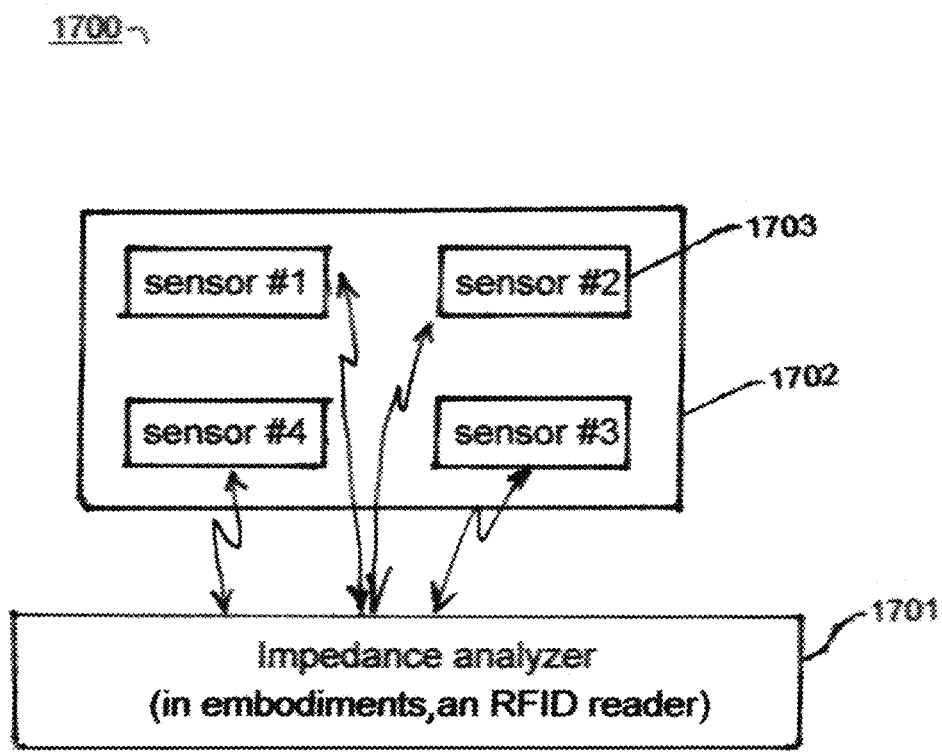
FIG. 17 is a schematic depicting an impedance spectrometer having wireless communication implemented with multiple RFID transponders and multiple analyte sensing elements disposed on a single sensing chip.

FIG. 17 is a schematic depicting a wireless-type impedance spectrometer 1700 with a means of wireless readout in accordance with the present teachings. The impedance analyzer 1701 interrogates individual analyte sensor elements 1703 within impedance sensor 1701. The wireless interrogation link may comprise an electric, magnetic or electromagnetic field-coupling.

Figure 18A:
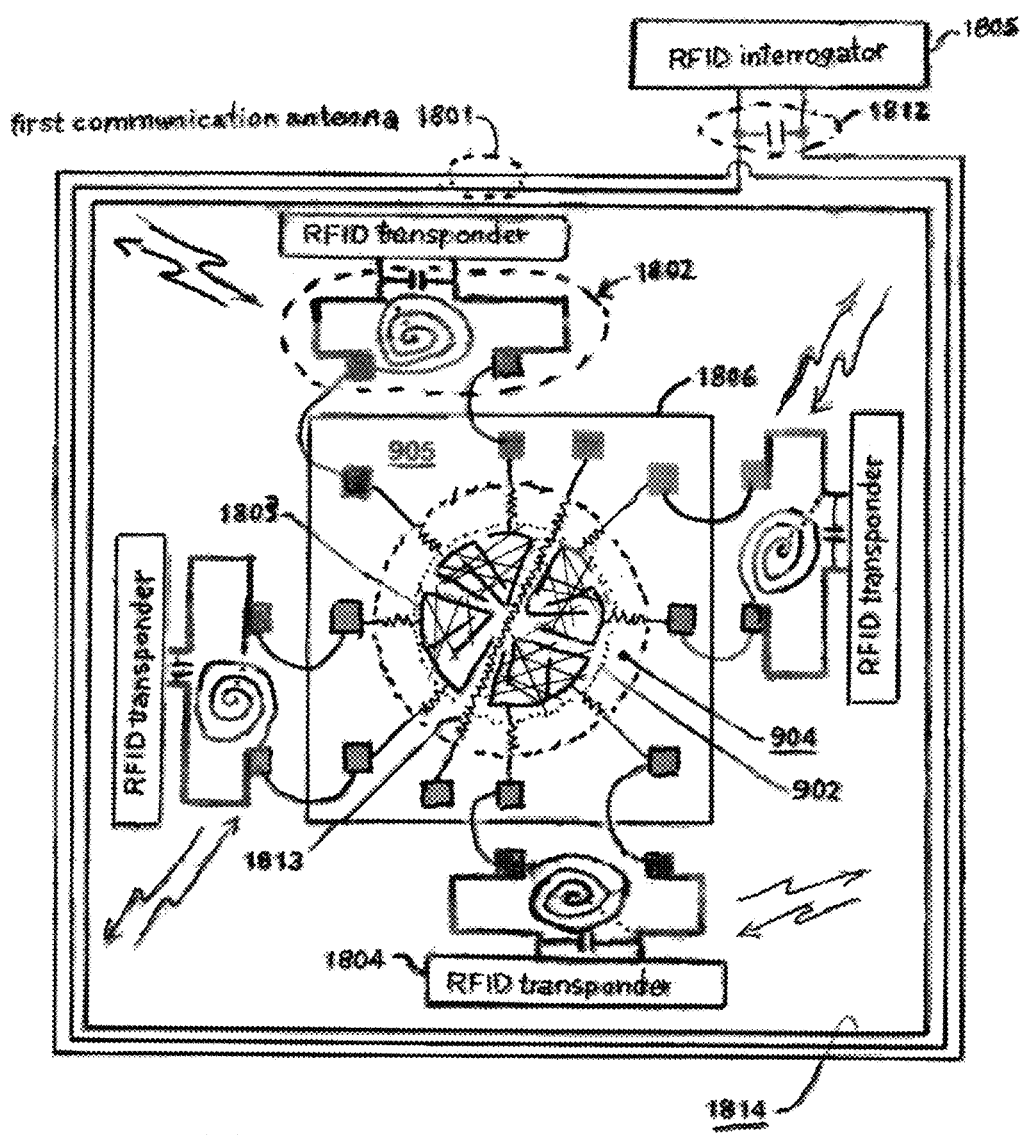
FIG. 18A depicts a wireless-type spectrometer comprised of a multi-sensor element impedence sensor comprised of a printed circuit board further comprised of multi-element analyte sensor in accordance with the present teachings.

FIG. 18A depicts a wireless-type impedance spectrometer comprised of an impedance analyzer 1701 and a multi-sensor element impedance sensor 1702. Typically, all sensor elements 1803 are exposed to the same analyte and, in some embodiments, each sensor element is sensitive to a different component of the exposed analyte. The impedance analyzer 1701 is comprised of RFID interrogator 1805 and an LC resonant antenna formed of inductor 1801 and capacitor 1812. The impedance sensor 1702 is comprised of four separate analyte sensors each communicating separately with the impedance analyzer 1701. The impedance sensor 1702 is comprised of printed circuit board 1814 further comprised of a sensing chip 1806, multiple second communication antennas 1802 and multiple RFID transponders 1804. Each individual sensor 1703 is comprised of an RC sensor element 1803, a second communication antenna 1802 and an RFID transponder 1804. Wireless communication is provided through coupling of the first communication antenna 1801 and a second communication antenna 1802. The two antennas are field-coupled through a magnetic, electric or electromagnetic field operating within the frequency range 100 kHz to 10 GHz.

In embodiments with 1800, all antennas are tuned to similar frequencies. In embodiments, the frequency of the impedance analyzer and/or the resonant frequency of each sensor antenna is programmable. In other embodiments, either or both the interrogator and sensor antenna not tuned.

In embodiments of FIG. 18A, the RFID interrogator 1805 receives a reflected RSSI signal from the LCR antenna 1802 wherein the RSSI signals are modulated by the field-coupling of a sensor element 1803 with the analyte. The amplitude of the reflected RSSI signal received by the RFID interrogator 1805 is processed to provide analyte identification and monitoring information. In embodiments, the RFID interrogator reader 1805 sources with a frequency $f_a$ which is scanned over a limited frequency range which includes the resonant frequency of the LCR antenna 1802 on the printed circuit board.

Figure 18B:
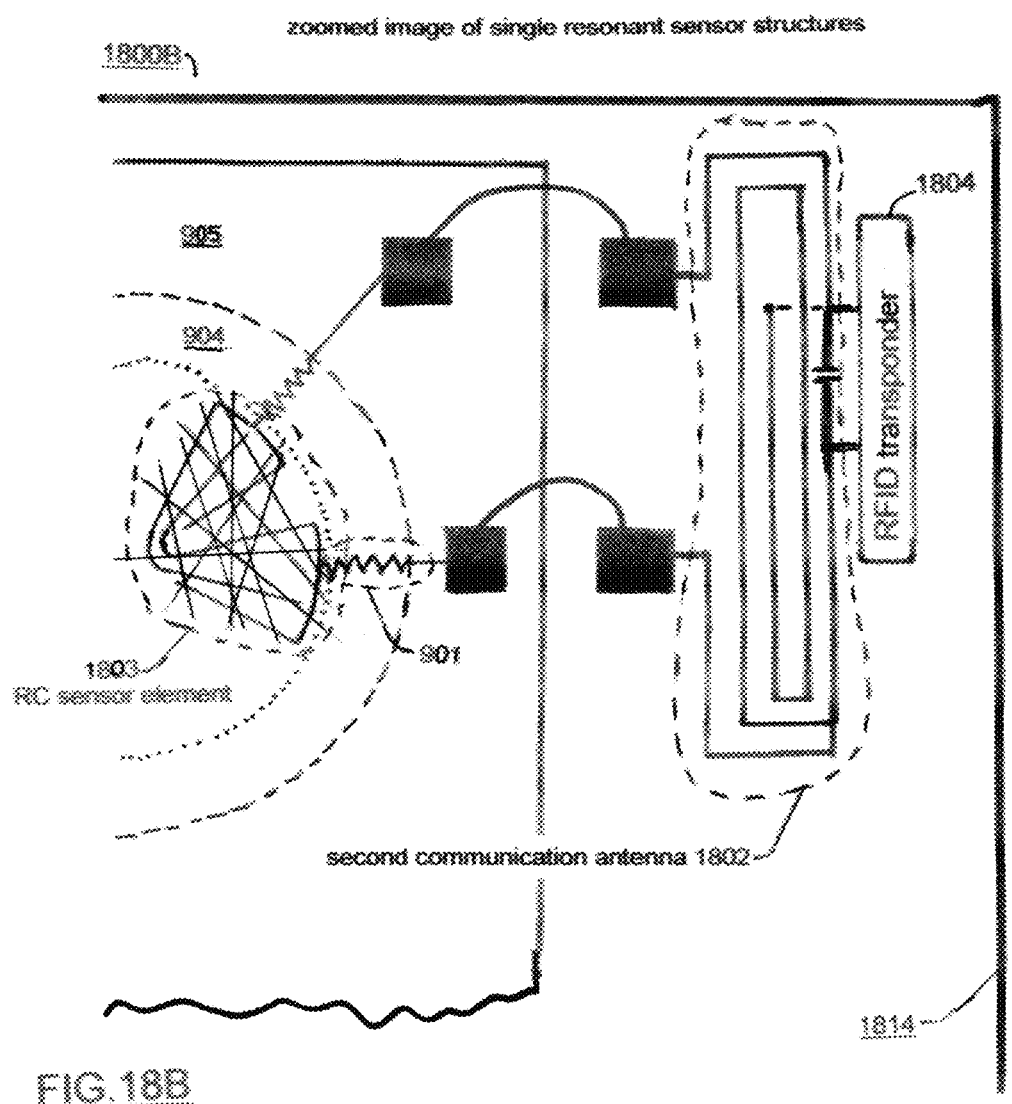
FIG. 18B depicts an enlarged view of a single impedance sensor from within the impedance sensor printed circuit board of FIG. 18A.

FIG. 18B depicts an enlarged view of one of the four impedance sensors 1703 of FIG. 18A as disposed on printed circuit board 1814. The impedance sensor 1703 is tuned by the LCR resonant circuit comprised of RC sensor element 1803 and second communication antenna 1802. Field coupling between the analyte and sensor element 1803 modulates the tuned impedance of LCR resonant circuit and further modulates the RSSI signal as received and processed by the RFID interrogator 1805.

In embodiments, the impedance spectrometer may be operated to identify and monitor an analyte based on a determination of analyte freezing, frost or boiling temperature. The impedance sensor 900 depicted in FIG. 9, physically configured within a wired-type of spectrometer, can be used for this purpose. For example, the freezing frost, and boiling temperature of a liquid analyte disposed on the micro-platform 902 is determined by monitoring the rate of cooling or heating of the micro-form which changes abruptly at freezing or boiling temperature. Freezing is accompanied by the heat of fusion which slows down the rate of cooling as ice or frost is formed on the interdigitated capacitor element 908. At boiling temperature the rate of temperature increase slows down. These critical temperature points are determined by monitoring the micro-platform 902 cooling and heating transient. In this embodiment, the on-platform thermistor is also used to heat the micro-platform. The thermoelectric array 911 is operated to provide a temperature Peltier cooling element. In applications, a determination of freezing and boiling temperatures provides in some applications a unique identification of a liquid analyte. In other embodiments, the impedance spectrometer is physically configured with additional sensor elements such as a chemi-resistor or a chemFET wherein the micro-platform temperature is maintained over a nominal range without freezing or boiling.

In an exemplary example the impedance spectrometer is physically configured with capacitor sensor element 900 of FIG. 9 to provide a dew point hygrometer. In this embodiment, the micro-platform 902 temperature is determined at the cooling point wherein ice or frost forms. As water condenses or freezes onto the capacitor sensor element 908, the rate of cooling change at dew or frost point temperature slows providing a means of specifying the dew or frost point temperature. Ambient analyte temperature is monitored with thermistor 906. In this embodiment, the impedance analyzer determines rate of temperature change for the micro-platform 908 to determine the freezing or frost temperature of the analyte.

In another hygrometer embodiment, the permittivity of exposed analyte is monitored. At dew point or frost point temperature, the imaginary component (capacitance related) of the analyte sensor element increases significantly indicating an increase in analyte dielectric constant. In both embodiments, the dew point or frost point temperature uniquely defines the humidity of the analyte gas or vapor based on spectrometer calibrations and algorithms. Dew and frost point temperature calibrations are readily available for humid gas and vapor analytes.

It is to be understood that although the disclosure teaches many examples of embodiments in accordance with the present teachings, many additional variations of the invention can easily be devised by those skilled in the art after reading this disclosure. As a consequence, the scope of the present invention is to be determined by the following claims.

What is claimed:

1. An impedance spectrometer comprising an impedance sensor and an impedance analyzer wherein the impedance sensor comprises a thermal micro-platform and wherein:
   the thermal micro-platform is formed of a device layer and supported by nanowires wherein the nanowires are partially disposed on a surrounding support platform;
   wherein the nanowires are physically configured with nano-dimensioned phononic structures to provide a reduction in thermal conductivity;
   the impedance sensor is comprised of an analyte sensing element, a temperature control element and a temperature sensing element; and
   the spectrometer providing a means for identifying and monitoring an exposed analyte gas, vapor, solid, or liquid.

2. The spectrometer of claim 1 providing a coupling between the analyte sensing element and the analyte wherein the coupling includes one or more of a resistive coupling and electric, magnetic or electromagnetic field coupling.

3. The spectrometer of claim 1 wherein the impedance sensor is physically comprised of one or more of an inductor, capacitor, resistor, RF antenna, RFID transponder and combinations thereof.

4. The spectrometer of claim 1 wherein the impedance sensor is physically configured as a passive or active sensor.

5. The spectrometer of claim 1 wherein the impedance analyzer interrogates the impedance sensor by wired or wireless means and with a signal at one or more of RF frequencies, one or more RF power levels and at one or more times.

6. The spectrometer of claim 1 wherein the analyte sensing element is activated with a material selected from a group including one or more of $WO_3$, $TiO_2$, $In_2O_3$, $CeO_2$, $ZnO_2$, $V_2O_3$, $MoS_2$, $In_2O_3$, CdS, PbS, $SnO_2$, InSb, $In_xS_{n_y}O_2$, graphene, nanotubes, organic charge donors, organic charge acceptors, noble metal catalysts and combinations thereof.

7. The spectrometer of claim 1 wherein the impedance analyzer is comprised of an RFID interrogator reader further comprised of an RF transmitter and receiver field-coupled with the impedance sensor wherein the receiver provides a measure of a return signal strength intensity RSSI and/or phase delay PD obtained from the RF transmitted signal which is reflected from the impedance sensor.

8. The spectrometer of claim 1 wherein the impedance analyzer is comprised of an RF signal source and a waveform analyzer with a wired or wireless connection to the impedance sensor.

9. The spectrometer of claim 1 wherein the impedance analyzer is comprised of a programmed controller for processing an interrogation measurement of one or more of RSSI, the anti-resonant frequency of the imaginary part of the impedance, the zero-reactance frequency of the real part of the sensor impedance and other components determined by the real and/or imaginary values of the analyte bulk permittivity.

10. The spectrometer of claim 1 wherein the impedance analyzer is comprised of a programmed controller for an interrogation measurement of one or more of steady state responses, transient responses varying power levels within one or more interrogation intervals.

11. The spectrometer of claim 1 wherein the temperature control element is comprised of one or more of a metal film heater, semiconductor film heater and a Peltier thermoelectric cooling device.

12. The spectrometer of claim 1 wherein the temperature sensing element is comprised of one or more of a metal film thermistor, semiconductor film thermistor, Seebeck thermoelectric device, bandgap diode MOS transistor (MOST) and bipolar transistor.

13. The spectrometer of claim 1 wherein the analyte sensing element, the temperature control element and the temperature sensing element are comprised of the same single physical structure.

14. The spectrometer of claim 1 wherein the impedance sensor is comprised of an energy harvesting unit further comprised of one or more of RF harvesting and photonic harvesting devices.

15. The spectrometer of claim 1 physically configured with a thermoelectric cooler wherein the analyte is a humid gas or vapor and the real part of bulk permittivity of condensed water, frost or ice is monitored to provide a sensor for $H_2O$.

16. The spectrometer of claim 1 wherein the analyte sensing element provides sensitivity to one or more of analytes including $H_2$, $H_2C_2$, $H_2O$, CO, $CO_2$, $CCl_4$, $NH_3$, $H_2S$, NO, $NO_2$, $AsH_3$, $SO_2$, $Ga_2O_3$, $BBr_3$, $SiH_4$, $H_2O_2$, $O_3$, HCl, humid air and organic compounds.

17. The spectrometer of claim 1 wherein the nanowire is comprised of a semiconductor further comprised of one or more of Si, Ge, SiGe, $ZnO_2$, GaAs, GaN, $Bi_2Te_3$, $CoSb_3$, $Sb_2Te_3$, $La_3Te_4$, SiC, GaN, $Sb_x)_2Te_3$ and binary/ternary alloys thereof.

18. The spectrometer of claim 1 wherein the microplatform and nanowires are comprised of the semiconductor device layer formed from a silicon semiconductor-on-oxide (SOI) starting wafer.

19. The spectrometer of claim 1 wherein the impedance analyzer is comprised of signal and data processing components including a microcontroller and memory programmed with algorithms and lookup tables to provide a means identifying and monitoring the analyte.

20. The spectrometer of claim 1 wherein the impedance spectrometer is communicating with, physically wired-to, disposed-within, or comprised of a mobile phone.

21. A method for measuring both the real and imaginary components of the bulk permittivity of the analyte using an impedance spectrometer according to claim 1, the method comprising:
   (i) a first measurement of the signal level from the impedance sensor coupled to the analyte at a frequency $f_1$ removed from the resonant frequency $f_0$ of the sensor element;
   (ii) a second measurement of the signal level from the impedance sensor coupled to an analyte at the resonant frequency $f_0$;
   (iii) wherein the interrogation frequency $f_a$ of the impedance analyzer and/or the primary resonant frequency $f_0$ of the impedance sensor is controlled;
   (iv) wherein a determination of the real and imaginary components of bulk permittivity of the analyte is provided by the impedance analyzer based on the first and second measurements together with repetitive and iterative combinations thereof; and
   (v) wherein the determination of the real and imaginary components of bulk permittivity of the analyte is further processed by the impedance analyzer to provide an identification and monitoring of the analyte of interest.

* * * * *